(12) United States Patent
Hanuka et al.

(10) Patent No.: US 9,345,612 B2
(45) Date of Patent: May 24, 2016

(54) OSTOMY APPLIANCE

(71) Applicant: B. Braun Medical SAS, Boulogne-Billancourt (FR)

(72) Inventors: David Hanuka, Ramat-Yishai (IL); Meir Or, Kfar Eschchar (IL); Hadas Ziso, Kiryat-Tivon (IL)

(73) Assignee: B. Braun Medical SAS, Boulogne-Billancourt (FR)

( * ) Notice: Subject to any disclaimer, the term of this patent is extended or adjusted under 35 U.S.C. 154(b) by 160 days.

(21) Appl. No.: 13/890,433

(22) Filed: May 9, 2013

(65) Prior Publication Data

US 2013/0304008 A1 Nov. 14, 2013

Related U.S. Application Data

(60) Provisional application No. 61/645,118, filed on May 10, 2012.

(51) Int. Cl.
| | |
|---|---|
| *A61F 5/448* | (2006.01) |
| *A61F 5/44* | (2006.01) |
| *A61F 5/442* | (2006.01) |
| *A61F 5/445* | (2006.01) |
| *A61F 5/441* | (2006.01) |

(52) U.S. Cl.
CPC ............ *A61F 5/4407* (2013.01); *A61F 5/4401* (2013.01); *A61F 5/441* (2013.01); *A61F 5/442* (2013.01); *A61F 5/4404* (2013.01); *A61F 5/445* (2013.01); *A61F 5/4405* (2013.01); *A61F 5/448* (2013.01); *A61F 2005/4402* (2013.01); *A61F 2005/4415* (2013.01)

(58) Field of Classification Search
CPC ...... A61F 5/4407; A61F 5/4408; A61F 5/448; A61F 2005/4483; A61F 2005/4486
USPC ................................................ 604/341, 342
See application file for complete search history.

(56) References Cited

U.S. PATENT DOCUMENTS

| | | | |
|---|---|---|---|
| 2,243,529 | A | 5/1941 | Grossman et al. |
| 2,341,984 | A | 2/1944 | Graves |
| 2,510,766 | A | 6/1950 | Surface |
| 2,544,579 | A | 3/1951 | Ardner |
| 2,639,710 | A | 5/1953 | Fazio |
| 2,667,167 | A | 1/1954 | Raiche |

(Continued)

FOREIGN PATENT DOCUMENTS

| | | |
|---|---|---|
| CN | 1 694661 | 11/2005 |
| DE | 19921555 | 2/2000 |

(Continued)

OTHER PUBLICATIONS

Applicant-Initiated Interview Summary Dated Dec. 13, 2013 From the US Patent and Trademark Office Re. U.S. Appl. No. 13/666,244.

(Continued)

*Primary Examiner* — Susan Su
(74) *Attorney, Agent, or Firm* — Kristina Bieker-Brady; Clark & Elbing LLP

(57) ABSTRACT

Ostomy appliance components for cleaning and related maintenance of a surgical stoma. Components take the form of attachments, inserted elements, and/or separate parts in contact with ostomy ports, wafers, and/or other connecting components.

8 Claims, 28 Drawing Sheets

(56) References Cited

U.S. PATENT DOCUMENTS

| | | |
|---|---|---|
| 2,971,510 A | 2/1961 | Berger |
| 3,398,744 A | 8/1968 | Hooper |
| 3,447,533 A | 6/1969 | Spicer |
| 3,718,141 A | 2/1973 | Goetz |
| 3,976,076 A | 8/1976 | Beach |
| 4,030,500 A | 6/1977 | Ronnquist |
| 4,121,589 A | 10/1978 | McDonnell |
| 4,170,231 A | 10/1979 | Collins |
| 4,183,357 A | 1/1980 | Bentley et al. |
| 4,209,010 A | 6/1980 | Ward et al. |
| 4,210,131 A | 7/1980 | Perlin |
| 4,217,664 A | 8/1980 | Faso |
| 4,232,672 A | 11/1980 | Steer et al. |
| 4,265,244 A | 5/1981 | Hill |
| 4,338,937 A | 7/1982 | Lerman |
| 4,344,434 A | 8/1982 | Robertson |
| 4,351,322 A | 9/1982 | Prager |
| 4,381,765 A | 5/1983 | Burton |
| 4,399,809 A | 8/1983 | Baro et al. |
| 4,421,124 A | 12/1983 | Marshall |
| 4,460,363 A | 7/1984 | Steer et al. |
| 4,462,510 A | 7/1984 | Steer et al. |
| 4,534,761 A | 8/1985 | Raible |
| 4,634,421 A | 1/1987 | Hegemann |
| 4,642,107 A | 2/1987 | Arnone et al. |
| 4,662,890 A | 5/1987 | Burton et al. |
| 4,721,508 A | 1/1988 | Burton |
| 4,786,283 A | 11/1988 | Andersson |
| 4,804,375 A | 2/1989 | Robertson |
| 4,810,250 A | 3/1989 | Ellenberg et al. |
| 4,834,731 A | 5/1989 | Nowak et al. |
| 4,854,316 A | 8/1989 | Davis |
| 4,863,447 A | 9/1989 | Smith |
| 4,941,869 A | 7/1990 | D'Amico |
| 4,950,223 A * | 8/1990 | Silvanov |
| 4,981,465 A | 1/1991 | Ballan et al. |
| 5,004,464 A | 4/1991 | Leise, Jr. |
| 5,026,360 A | 6/1991 | Johnson et al. |
| 5,045,052 A | 9/1991 | Sans |
| 5,108,430 A | 4/1992 | Ravo |
| 5,125,916 A | 6/1992 | Panebianco et al. |
| 5,135,519 A | 8/1992 | Helmer |
| 5,163,897 A | 11/1992 | Persky |
| 5,163,930 A | 11/1992 | Blum |
| 5,261,898 A | 11/1993 | Polin et al. |
| 5,269,774 A | 12/1993 | Gray |
| 5,372,594 A | 12/1994 | Colacello et al. |
| 5,401,264 A | 3/1995 | Leise, Jr. |
| 5,501,678 A | 3/1996 | Olsen |
| 5,549,588 A | 8/1996 | Johnson |
| 5,569,216 A | 10/1996 | Kim |
| 5,658,266 A | 8/1997 | Colacello et al. |
| 5,683,372 A | 11/1997 | Colacello et al. |
| 5,771,590 A | 6/1998 | Colacello et al. |
| 5,785,677 A | 7/1998 | Auweiler |
| 5,785,695 A * | 7/1998 | Sato ........................ A61F 5/448 604/338 |
| 5,947,942 A | 9/1999 | Galjour |
| 6,033,390 A | 3/2000 | Von Dyck |
| 6,050,982 A | 4/2000 | Wheeler |
| 6,071,268 A | 6/2000 | Wagner |
| 6,329,465 B1 | 12/2001 | Takahashi et al. |
| 6,350,255 B1 | 2/2002 | Von Dyck |
| 6,357,445 B1 | 3/2002 | Shaw |
| 6,481,589 B2 | 11/2002 | Blomdahl et al. |
| 6,485,476 B1 | 11/2002 | Von Dyck et al. |
| 6,589,222 B1 | 7/2003 | Olsen |
| 6,595,971 B1 | 7/2003 | Von Dyck et al. |
| 6,659,988 B1 | 12/2003 | Steer et al. |
| 6,689,111 B2 | 2/2004 | Mulhauser et al. |
| 6,695,825 B2 | 2/2004 | Castles |
| 6,723,079 B2 | 4/2004 | Cline |
| 6,963,772 B2 | 11/2005 | Bloom et al. |
| 7,001,367 B2 | 2/2006 | Arkinstall |
| 7,083,569 B2 | 8/2006 | Boulanger et al. |
| 7,087,041 B2 | 8/2006 | Von Dyck et al. |
| 7,250,040 B2 | 7/2007 | Andersen |
| 7,314,443 B2 | 1/2008 | Jordan et al. |
| 7,582,072 B2 | 9/2009 | McMichael |
| 7,628,767 B1 * | 12/2009 | Simmons et al. ............... 602/79 |
| 7,670,289 B1 | 3/2010 | McCall |
| 7,722,586 B2 * | 5/2010 | Mullejans et al. ............ 604/342 |
| 7,857,796 B2 | 12/2010 | Cline et al. |
| 8,070,737 B2 | 12/2011 | Cline et al. |
| 8,092,437 B2 | 1/2012 | Cline |
| 8,100,875 B2 | 1/2012 | Cline et al. |
| 8,142,406 B2 | 3/2012 | Blum |
| 8,388,586 B2 | 3/2013 | Weig |
| 8,460,259 B2 | 6/2013 | Tsai |
| 8,690,848 B2 * | 4/2014 | Cason ............................ 604/342 |
| 8,821,464 B2 * | 9/2014 | Hanuka et al. ................. 604/333 |
| 8,821,465 B2 | 9/2014 | Hanuka et al. |
| 8,845,607 B2 | 9/2014 | Hanuka et al. |
| 8,858,519 B2 | 10/2014 | Hanuka et al. |
| 8,864,729 B2 | 10/2014 | Hanuka et al. |
| 8,900,116 B2 | 12/2014 | Hanuka et al. |
| 8,998,862 B2 * | 4/2015 | Hanuka et al. ................. 604/318 |
| 2003/0004477 A1 | 1/2003 | Nielsen et al. |
| 2003/0150050 A1 | 8/2003 | Tanaka et al. |
| 2003/0199783 A1 | 10/2003 | Bloom et al. |
| 2003/0220621 A1 * | 11/2003 | Arkinstall |
| 2004/0029467 A1 | 2/2004 | Lacroix |
| 2004/0073179 A1 * | 4/2004 | Andersen ....................... 604/338 |
| 2004/0122527 A1 | 6/2004 | Imran |
| 2004/0167376 A1 | 8/2004 | Peters et al. |
| 2004/0171999 A1 | 9/2004 | Andersen et al. |
| 2004/0181197 A1 | 9/2004 | Cline |
| 2004/0193122 A1 * | 9/2004 | Cline et al. .................... 604/332 |
| 2005/0027159 A1 | 2/2005 | Feng et al. |
| 2005/0054996 A1 | 3/2005 | Gregory |
| 2005/0065488 A1 | 3/2005 | Elliott |
| 2005/0104457 A1 | 5/2005 | Jordan et al. |
| 2005/0115857 A1 * | 6/2005 | Homann ....................... 206/509 |
| 2006/0048283 A1 | 3/2006 | Sorensen |
| 2006/0206069 A1 | 9/2006 | Cline |
| 2006/0229596 A1 | 10/2006 | Weiser et al. |
| 2007/0049878 A1 | 3/2007 | Kim et al. |
| 2007/0088300 A1 | 4/2007 | Cline et al. |
| 2007/0129695 A1 * | 6/2007 | Blum ....................... A61F 5/445 604/338 |
| 2007/0142780 A1 | 6/2007 | Van Lue |
| 2007/0191794 A1 | 8/2007 | Cline et al. |
| 2007/0219532 A1 | 9/2007 | Karpowicz et al. |
| 2007/0260206 A1 | 11/2007 | Mullejans et al. |
| 2007/0276346 A1 | 11/2007 | Poulsen et al. |
| 2008/0004580 A1 | 1/2008 | Mullejans et al. |
| 2008/0033380 A1 | 2/2008 | Andersen |
| 2008/0091154 A1 | 4/2008 | Botten |
| 2008/0108862 A1 | 5/2008 | Jordan et al. |
| 2008/0135044 A1 | 6/2008 | Freitag et al. |
| 2008/0269698 A1 | 10/2008 | Alexander et al. |
| 2008/0275410 A1 | 11/2008 | Burt |
| 2009/0043151 A1 | 2/2009 | Gobel |
| 2009/0216206 A1 | 8/2009 | Nishtala et al. |
| 2009/0247969 A1 | 10/2009 | Nishtala et al. |
| 2010/0069859 A1 | 3/2010 | Weig |
| 2010/0174253 A1 | 7/2010 | Cline et al. |
| 2011/0015475 A1 | 1/2011 | Hanuka et al. |
| 2011/0040231 A1 | 2/2011 | Gregory |
| 2011/0106032 A1 * | 5/2011 | Kratky ..................... A61F 5/448 604/337 |
| 2012/0109086 A1 * | 5/2012 | Tsai .............................. 604/335 |
| 2012/0136324 A1 | 5/2012 | Hanuka et al. |
| 2012/0179124 A1 * | 7/2012 | Nguyen-Demary et al. . 604/333 |
| 2012/0245535 A1 | 9/2012 | Jacobsson et al. |
| 2013/0053803 A1 * | 2/2013 | Willoughby ............ A61F 5/448 604/337 |
| 2013/0060212 A1 | 3/2013 | Hanuka et al. |
| 2013/0060213 A1 | 3/2013 | Hanuka et al. |
| 2013/0060214 A1 * | 3/2013 | Willoughby ............ A61F 5/448 604/338 |
| 2013/0079736 A1 | 3/2013 | Hanuka et al. |
| 2013/0079737 A1 | 3/2013 | Hanuka et al. |
| 2013/0079738 A1 | 3/2013 | Hanuka et al. |

(56) References Cited

U.S. PATENT DOCUMENTS

| | | | |
|---|---|---|---|
| 2013/0116642 | A1 | 5/2013 | Hanuka et al. |
| 2013/0304008 | A1 | 11/2013 | Hanuka et al. |
| 2015/0025488 | A1 | 1/2015 | Hanuka et al. |
| 2015/0057626 | A1 | 2/2015 | Hanuka et al. |
| 2015/0141944 | A1 | 5/2015 | Hanuka et al. |
| 2015/0305916 | A1 | 10/2015 | Hanuka et al. |

FOREIGN PATENT DOCUMENTS

| | | |
|---|---|---|
| DE | 102004001631 | 8/2004 |
| DE | 102007062133 | 7/2009 |
| EP | 1795157 | 6/2007 |
| EP | 2027835 | 2/2009 |
| FR | 2870112 | 11/2005 |
| GB | 2094153 | 9/1982 |
| JP | 2006-314479 | 11/2006 |
| JP | 2008-507308 | 3/2008 |
| WO | WO 87/03192 | 6/1987 |
| WO | WO 90/07311 | 7/1990 |
| WO | WO 96/32904 | 10/1996 |
| WO | WO 99/43277 | 9/1999 |
| WO | WO 01/49224 | 7/2001 |
| WO | WO 02/058603 | 8/2002 |
| WO | WO 03/065945 | 8/2003 |
| WO | WO 03/071997 | 9/2003 |
| WO | WO 2006/010556 | 2/2006 |
| WO | WO 2007/030703 | 3/2007 |
| WO | WO 2008/048856 | 4/2008 |
| WO | WO 2008/103789 | 8/2008 |
| WO | WO 2008/141180 | 11/2008 |
| WO | WO 2009/083183 | 7/2009 |
| WO | WO 2009/155537 | 12/2009 |
| WO | WO 2011/007355 | 1/2011 |
| WO | WO 2011/013872 | 2/2011 |
| WO | WO 2011/039517 | 4/2011 |
| WO | WO 2011/057635 | 5/2011 |
| WO | WO 2011/138727 | 11/2011 |
| WO | WO 2011/138728 | 11/2011 |
| WO | WO-2011/138730 A1 | 11/2011 |
| WO | WO 2011/138731 | 11/2011 |
| WO | WO 2013/022487 | 2/2013 |
| WO | WO 2013/168165 | 11/2013 |
| WO | WO 2014/081889 | 5/2014 |
| WO | WO 2014/181338 | 11/2014 |
| WO | WO 2014/181339 | 11/2014 |

OTHER PUBLICATIONS

Applicant-Initiated Interview Summary Dated Dec. 13, 2013 From the US Patent and Trademark Office Re. U.S. Appl. No. 13/666,513.
International Search Report and the Written Opinion Dated Dec. 20, 2013 From the International Searching Authority Re. Application No. PCT/IL2013/050401.
Notice of Allowance Dated Nov. 28, 2014 From the US Patent and Trademark Office Re. U.S. Appl. No. 13/384,343.
International Search Report and the Written Opinion Dated Dec. 19, 2014 From the International Searching Authority Re. Application No. PCT/IL2014/050416.
International Search Report and the Written Opinion Dated Dec. 19, 2014 From the International Searching Authority Re. Application No. PCT/IL2014/050417.
Communication Pursuant to Article 94(3) EPC Dated Dec. 17, 2013 From the European Patent Office Re. Application No. 11723672.9.
Communication Pursuant to Article 94(3) EPC Dated Dec. 19, 2013 From the European Patent Office Re. Application No. 11723674.5.
Communication Pursuant to Article 94(3) EPC Dated Dec. 19, 2013 From the European Patent Office Re. Application No. 11724783.3.
Official Action Dated Jan. 14, 2014 From the US Patent and Trademark Office Re. U.S. Appl. No. 13/680,161.
Applicant-Initiated Interview Summary Dated Jan. 27, 2014 From the US Patent and Trademark Office Re. U.S. Appl. No. 13/384,343.
Advisory Action Before the Filing of an Appeal Brief Dated Feb. 4, 2014 From the US Patent and Trademark Office Re. U.S. Appl. No. 12/835,838.

Official Action Dated Jan. 26, 2015 From the US Patent and Trademark Office Re. U.S. Appl. No. 13/666,244.
Communication Relating to the Results of the Partial International Search Dated Sep. 16, 2013 From the International Searching Authority Re. Application No. PCT/IL2013/050401.
Notice of Allowance Dated Feb. 18, 2014 From the US Patent and Trademark Office Re. U.S. Appl. No. 13/666,513.
Communication Pursuant to Article 94(3) EPC Dated Jan. 27, 2015 From the European Patent Office Re. Application No. 11723674.5.
Notice of Allowance Dated Mar. 18, 2014 From the US Patent and Trademark Office Re. U.S. Appl. No. 13/666,178.
Advisory Action Before the Filing of an Appeal Brief Dated Mar. 31, 2014 From the US Patent and Trademark Office Re. U.S. Appl. No. 13/384,343.
Notice of Allowance Dated Apr. 4, 2014 From the US Patent and Trademark Office Re. U.S. Appl. No. 13/680,169.
Applicant-Initiated Interview Summary Dated Apr. 14, 2014 From the US Patent and Trademark Office Re. U.S. Appl. No. 13/384,343.
Notice of Allowance Dated Apr. 29, 2014 From the US Patent and Trademark Office Re. U.S. Appl. No. 13/680,161.
Translation Dated Dec. 15, 2014 of Notification of Office Action Dated Dec. 2, 2014 From the State Intellectual Property Office of the People's Republic of China Re. Application No. 201180033 1827.
Notice of Allowance Dated May 8, 2014 From the US Patent and Trademark Office Re. U.S. Appl. No. 13/666,461.
Notice of Reason for Rejection Dated Apr. 15, 2014 From the Japanese Patent Office Re. Application No. 2012-520149 and Its Translation Into English.
Zhang et al. "Occlusion Effect Comparison of Artificial Silicone Rubber Closure Devices With Different Diameters", Chinese Journal of Tissue Engineering Research, 16(8): 1496-1500, Feb. 19, 2012. Abstract in English.
Communication Under Rule 71(3) EPC Dated May 19, 2014 From the European Patent Office Re. Application No. 10747082.5.
Notification of Office Action Dated May 6, 2014 From the State Intellectual Property Office of the People's Republic of China Re. Application No. 201180033 1827 and Its Translation Into English.
Search Report Dated May 6, 2014 From the State Intellectual Property Office of the People's Republic of China Re. Application No. 201180033 1827 and Its Translation Into English.
Supplemental Notice of Allowability Dated May 21, 2014 From the US Patent and Trademark Office Re. U.S. Appl. No. 13/666,513.
Notice of Allowance Dated Jun. 2, 2014 From the US Patent and Trademark Office Re. U.S. Appl. No. 13/666,178.
Supplemental Notice of Allowability Dated Jun. 23, 2014 From the US Patent and Trademark Office Re. U.S. Appl. No. 13/666,513.
Notification of Office Action Dated May 27, 2014 From the State Intellectual Property Office of the People's Republic of China Re. Application No. 201180033162.X.
Official Action Dated Jun. 26, 2014 From the US Patent and Trademark Office Re. U.S. Appl. No. 13/384,343.
Supplemental Notice of Allowability Dated Jun. 23, 2014 From the US Patent and Trademark Office Re. U.S. Appl. No. 13/680,161.
Supplemental Notice of Allowability Dated Jun. 27, 2014 From the US Patent and Trademark Office Re. U.S. Appl. No. 13/680,169.
Corrected Notice of Allowability Dated Jul. 8, 2014 From the US Patent and Trademark Office Re. U.S. Appl. No. 13/666,461.
Corrected Notice of Allowability Dated Jul. 22, 2014 From the US Patent and Trademark Office Re. U.S. Appl. No. 13/666,513.
Supplemental Notice of Allowability Dated Jul. 22, 2014 From the US Patent and Trademark Office Re. U.S. Appl. No. 13/680,169.
Supplemental Notice of Allowability Dated Jul. 23, 2014 From the US Patent and Trademark Office Re. U.S. Appl. No. 13/666,461.
Supplemental Notice of Allowability Dated Jul. 25, 2014 From the US Patent and Trademark Office Re. U.S. Appl. No. 13/680,161.
Official Action Dated Jul. 29, 2014 From the US Patent and Trademark Office Re. U.S. Appl. No. 13/666,244.
Supplemental Notice of Allowability Dated Sep. 16, 2014 From the US Patent and Trademark Office Re. U.S. Appl. No. 13/666,461.
Supplemental Notice of Allowability Dated Sep. 16, 2014 From the US Patent and Trademark Office Re. U.S. Appl. No. 13/680,161.
Applicant-Initiated Interview Summary Dated Jul. 25, 2013 From the US Patent and Trademark Office Re. U.S. Appl. No. 13/680,161.

(56) References Cited

OTHER PUBLICATIONS

Applicant-Initiated Interview Summary Dated Jul. 26, 2013 From the US Patent and Trademark Office Re. U.S. Appl. No. 13/666,513.
Applicant-Initiated Interview Summary Dated Jul. 26, 2013 From the US Patent and Trademark Office Re. U.S. Appl. No. 13/680,169.
Communication Pursuant to Article 94(3) EPC Dated Feb. 11, 2013 From the European Patent Office Re. Application No. 10747082.5.
Communication Relating to the Results of the Partial International Search Dated Aug. 12, 2011 From the International Searching Authority Re. Application No. PCT/IB2011/051932.
Communication Relating to the Results of the Partial International Search Dated Aug. 16, 2011 From the International Searching Authority Re. Application No. PCT/IB2011/051933.
Communication Relating to the Results of the Partial International Search Dated Nov. 17, 2010 From the International Searching Authority Re. Application No. PCT/IL2010/000565.
Communication Relating to the Results of the Partial International Search Dated Aug. 18, 2011 From the International Searching Authority Re: Application No. PCT/IB2011/051938.
International Preliminary Report on Patentability Dated Jun. 1, 2012 From the International Preliminary Examining Authority Re. Application No. PCT/IB2011/051933.
International Preliminary Report on Patentability Dated Jun. 5, 2012 From the International Preliminary Examining Authority Re. Application No. PCT/IB2011/051932.
International Preliminary Report on Patentability Dated Sep. 6, 2012 From the International Preliminary Examining Authority Re. Application No. PCT/IB2011/051938.
International Preliminary Report on Patentability Dated Nov. 15, 2012 From the International Bureau of WIPO Re. Application No. PCT/IB2011/051936.
International Preliminary Report on Patentability Dated Oct. 31, 2011 From the International Preliminary Examining Authority Re. Application No. PCT/IL2010/000565.
International Search Report and the Written Opinion Dated Oct. 14, 2011 From the International Searching Authority Re. Application No. PCT/IB2011/051933.
International Search Report and the Written Opinion Dated Oct. 17, 2011 From the International Searching Authority Re. Application No. PCT/IB2011/051932.
International Search Report and the Written Opinion Dated Aug. 18, 2011 From the International Searching Authority Re. Application No. PCT/IB2011/051936.
International Search Report and the Written Opinion Dated Oct. 19, 2011 From the International Searching Authority Re: Application No. PCT/IB2011/051938.
International Search Report and the Written Opinion Dated Feb. 28, 2011 From the International Searching Authority Re. Application No. PCT/IL2010/000565.
Invitation to Pay Additional Fees Dated Oct. 7, 2011 From the International Preliminary Examining Authority Re. Application No. PCT/IL2010/000565.
Notification Concerning Informal Communications With the Applicant Dated May 3, 2012 From the International Searching Authority Re: Application No. PCT/IB2011/051938.
Notification Concerning Informal Communications With the Applicant Dated May 4, 2012 From the International Searching Authority Re: Application No. PCT/IB2011/051933.
Notification Concerning Informal Communications With the Applicant Dated May 18, 2012 From the International Searching Authority Re: Application No. PCT/IB2011/051932.
Official Action Dated Jul. 1, 2013 From the US Patent and Trademark Office Re. U.S. Appl. No. 13/384,343.
Official Action Dated Mar. 5, 2013 From the US Patent and Trademark Office Re. U.S. Appl. No. 13/666,513.
Official Action Dated May 9, 2013 From the US Patent and Trademark Office Re. U.S. Appl. No. 13/666,461.
Official Action Dated Jul. 10, 2013 From the US Patent and Trademark Office Re. U.S. Appl. No. 13/680,169.
Official Action Dated Jul. 11, 2013 From the US Patent and Trademark Office Re. U.S. Appl. No. 13/680,161.
Official Action Dated Mar. 25, 2013 From the US Patent and Trademark Office Re. U.S. Appl. No. 13/666,178.
Official Action Dated Aug. 29, 2013 From the US Patent and Trademark Office Re. U.S. Appl. No. 12/835,838.
Official Action Dated Jan. 30, 2013 From the US Patent and Trademark Office Re. U.S. Appl. No. 12/835,838.
Response Dated May 30, 2011 to the Written Opinion of Feb. 28, 2011 From the International Searching Authority Re. Application No. PCT/IL2010/000565.
Restriction Official Action Dated Oct. 15, 2012 From the US Patent and Trademark Office Re. U.S. Appl. No. 12/835,838.
Translation of Notification of Office Action Dated Jul. 30, 2013 From the State Intellectual Property Office of the People's Republic of China Re. Application No. 201080032032.X.
Written Opinion Dated Jun. 1, 2012 From the International Preliminary Examining Authority Re. Application No. PCT/IB2011/051938.
Communication Relating to the Results of the Partial International Search Dated Sep. 16, 2014 From the International Searching Authority Re. Application No. PCT/IL2014/050416.
Notice of Allowance Dated Oct. 1, 2014 From the US Patent and Trademark Office Re. U.S. Appl. No. 12/835,838.
Communication Relating to the Results of the Partial International Search Dated Sep. 16, 2014 From the International Searching Authority Re. Application No. PCT/IL2014/050417.
Official Action Dated Oct. 16, 2013 From the US Patent and Trademark Office Re. U.S. Appl. No. 13/666,244.
Official Action Dated Oct. 16, 2013 From the US Patent and Trademark Office Re. U.S. Appl. No. 13/666,513.
Official Action Dated Oct. 18, 2013 From the US Patent and Trademark Office Re. U.S. Appl. No. 13/384,343.
Notification of Office Action and Search Report Dated Oct. 20, 2014 From the State Intellectual Property Office of the People's Republic of China Re. Application No. 201080032032.X and Its Translation Into English.
Official Action Dated Nov. 7, 2013 From the US Patent and Trademark Office Re. U.S. Appl. No. 13/666,178.
Official Action Dated Nov. 7, 2013 From the US Patent and Trademark Office Re. U.S. Appl. No. 13/680,169.
International Preliminary Report on Patentability Dated Nov. 20, 2014 From the International Bureau of WIPO Re. Application No. PCT/IL2013/050401.
Official Action Dated Nov. 13, 2013 From the US Patent and Trademark Office Re. U.S. Appl. No. 13/666,461.
Communication Pursuant to Article 94(3) EPC Dated Nov. 5, 2014 From the European Patent Office Re. Application No. 11724783.3.
Summons to Attend Oral Proceedings Pursuant to Rule 115(1) EPC Dated Nov. 22, 2013 From the European Patent Office Re. Application No. 10747082.5.
Notification of Office Action Dated Dec. 2, 2014 From the State Intellectual Property Office of the People's Republic of China Re. Application No. 2011800331827.
Notification of Office Action Dated Apr. 18, 2014 From the State Intellectual Property Office of the People's Republic of China Re. Application No. 201080032032.X and Its Translation Into English.
Search Report Dated Apr. 18, 2014 From the State Intellectual Property Office of the People's Republic of China Re. Application No. 201080032032.X and Its Translation Into English.

\* cited by examiner

OSTOMY APPLIANCE

RELATED APPLICATIONS

This application claims the benefit of priority under 35 USC §119(e) of U.S. Provisional Patent Application No. 61/645,118 filed May 10, 2012, the contents of which are incorporated herein by reference in their entirety. This application is related to International Patent Application No. PCT/IB2011/051938 filed May 2, 2011.

FIELD AND BACKGROUND OF THE INVENTION

The present invention, in some embodiments thereof, relates to the field of surgically created openings for stomal discharge removal (stoma) in living subjects, and more particularly, to devices and methods for covering a stoma as may be used in the case of a colostomy, ileostomy or urostomy.

In performing an ostomy, the physician will generally form the stoma in the abdominal wall and attach an end or a side of a healthy portion of the intestine (large or small intestine, depending on the type of ostomy) to the stoma from the visceral side of the abdominal wall or, alternatively, pass the intestinal portion through the stoma and attach it to the outside of the abdominal wall. The stoma may be permanently left in a patient suffering from a condition for when it is no longer possible for the intestinal content to pass out via the anus, for example, due to colon cancer, diverticulitis, trauma, or inflammatory bowel disease; or may be temporary, as may be the case following an operation on a section of the bowel (small intestine and/or large intestine) requiring a healing period.

The use of an ostomy appliance is indicated for patients with a stoma, to help manage stomal discharge. According to the nature of the stoma, stomal discharge may comprise, for example, fecal matter, urine, and/or mucus. Appliances may be wholly external, or at least partially internal. Common elements of ostomy appliances include a pouch for collecting stomal discharge, and a means to seal the pouch over the stoma. In some cases, a plug or cover is used in addition to or in place of a pouch. Ostomy appliance designs described in the art include the following.

U.S. Pat. No. 7,250,040 relates to "an arrangement at a stoma bag of the type used by persons or animals with a colostoma, including a flexible bag (flexibag) and a ring fastener/magazine ring, where the ring fastener/magazine ring is designed to be connected to a stoma plate, and where, in its initial position, the entire flexibag is located in or in close proximity to the ring fastener/magazine ring."

U.S. Patent Application Publication Number 2004/0181197 relates to "a flexible membrane is situated within a rigid or semi-rigid cap. The edge of the cap wall is adhesively fixed to the tissue surrounding the stoma. The interior of the cap is pressurized to press the membrane to seal the stoma against the discharge of solid and semi-solid waste. Gas escapes through a vent with a filter element. The cap can be pressurized by an external pump or an integral pump member situated on top of the cap. A relief valve prevents over pressurization. A collection pouch can be provided as part of a device. The device can be removably mounted on a standard two-piece faceplate."

U.S. Patent Application Publication Number 2007/0088300 relates to "a single-use ostomy appliance is described including an ostomy coupling for releasable coupling first and second portions at a stomal orifice. The two portions may be separable body-side and non-body-side parts, or the two portions may be portions of a unitary ostomy device such as a controlled evacuation device. The coupling includes a mechanical fastener configured such that the coupling is rendered substantially not resecurable after the fastener is released."

U.S. Patent Application Publication Number 2007/0191794 relates to "a controlled evacuation ostomy appliance comprises a membrane that is urged into sealing engagement with a stoma, by the generation of radial tension in the membrane. A tensioning device applies tension, with respect to the stoma, at one or more positions that are (i) outboard of the periphery of the projecting portion of the stoma, and/or (ii) between the level of the peristomal skin and the level of the most projecting part of the stoma. Tension limiting means are disclosed. The membrane may be gas-permeable to allow flatus to be vented."

U.S. Pat. No. 6,689,111 relates to "a balloon-like member is received in the bowel and inflated to seal the stoma. The member includes a thin, flexible wall defining an opening. A rigid or semi-rigid cap retains the member and closes the opening in the member wall. Skin comfortable adhesive adheres the edge of the cap to the tissue surrounding the stoma. A flexible dilation tube facilitates insertion of the member and cooperates with a pump to inflate the member. The cap is preferably removably attached to a standard two-piece ostomy faceplate and is provided with a filter element to vent flatus."

SUMMARY OF THE INVENTION

According to an aspect of some embodiments of the present invention there is provided a flushing device for distributing fluid within an ostomy appliance worn over a surgical stoma, comprising: an annular body, sized and shaped to fittingly insert into the opening of the ostomy appliance; an attachment element for attaching the body to its inserted position; and a fluid delivery lumen passing into the annulus of the body having: an inlet sized and positioned to attach to a fluid source, and at least one outlet sized and positioned to deliver fluid to one or more predetermined locations.

According to some embodiments of the invention, the attachment to the ostomy appliance is sealed to prevent outflow of delivered fluid, except through the proximal end of the annular body.

According to some embodiments of the invention, the fitting insertion of the annular body of the device to the ostomy appliance is reversible.

According to some embodiments of the invention, there is provided a waste collection pouch in sealed fluid communication with the proximal end of the annular body.

According to some embodiments of the invention, the pouch is collapsed.

According to some embodiments of the invention, the proximal end of the annular body is closed.

According to some embodiments of the invention, the at least one outlet of the delivery lumen terminates external to the stoma when the annular body of the device is inserted into the ostomy appliance.

According to some embodiments of the invention, fluid delivery to the one or more predetermined locations of the stoma comprises washing at least a portion of the stoma.

According to some embodiments of the invention, fluid delivery to the one or more predetermined locations comprises washing at least a portion of the ostomy appliance.

According to some embodiments of the invention, fluid delivery to the one or more predetermined locations comprises softening fecal material accumulated in the ostomy appliance.

According to some embodiments of the invention, the at least one outlet of the delivery lumen terminates internal to the stoma when the annular body of the device is inserted into the ostomy appliance.

According to some embodiments of the invention, fluid delivery to the one or more predetermined locations of the stoma comprises injecting fluid into the space behind the stomal aperture.

According to some embodiments of the invention, the delivery lumen comprises a removable tubule at its distal end.

According to some embodiments of the invention, the fitting insertion of the annular body of the device to the ostomy appliance is sufficiently secure that irrigation does not dislodge it.

According to some embodiments of the invention, the fitting insertion of the annular body of the device to the ostomy appliance is sufficiently secure that it does not dislodge during ambulatory movement.

According to some embodiments of the invention, said attachment element is configured such that the annular body is interchangeable with an ostomy cap.

According to an aspect of some embodiments of the present invention there is provided a flushing element for distributing fluid within an ostomy appliance worn over a surgical stoma, comprising: a body, sized and shaped to fittingly occupy a cavity of the ostomy device; and at least one flushing channel comprising a void in the body, having: an inlet, positioned so that when the body is fitted to the cavity, the inlet receives and transmits pressurized fluid delivered from a fluid delivery port inside the cavity; and at least one outlet sized and positioned to deliver fluid received by the inlet to one or more predetermined locations.

According to some embodiments of the invention, the fluid delivery port receives fluid from a lumen passing in through a wall of the ostomy appliance.

According to some embodiments of the invention, the flushing element body fits within the ostomy appliance such that it acts as a seal resisting leakage from the stomal aperture to the exterior of the ostomy appliance.

According to some embodiments of the invention, the flushing element body fits within the ostomy appliance such that it acts as a seal resisting leakage from the stomal aperture to a region of the skin.

According to some embodiments of the invention, the flushing element body fits within the ostomy appliance such that it acts as a spacer occupying at least a portion of the space between the stoma and the ostomy appliance.

According to some embodiments of the invention, the material of the flushing element body comprises an elastomer.

According to some embodiments of the invention, the flushing channel comprises an internal lumen of the flushing element body.

According to some embodiments of the invention, the flushing channel comprises a depression in the surface of the flushing element body.

According to some embodiments of the invention, the at least one outlet connects to the interior of the cavity through at least one one-way valve.

According to some embodiments of the invention, the at least one outlet connects to the interior of the cavity through at least one slit.

According to some embodiments of the invention, the flushing element body comprises an annulus.

According to some embodiments of the invention, the flushing channel comprises a manifold.

According to some embodiments of the invention, the at least one outlet comprises a plurality of outlets.

According to some embodiments of the invention, at least two of the plurality of outlets are radially separated by at least one third of the circumference of the stoma.

According to an aspect of some embodiments of the present invention there is provided an insert for an ostomy appliance used with a surgical stoma comprising a pad of absorbent material fitted to be held at a predefined location within the ostomy appliance such that discharge material exiting the stoma contacts it.

According to some embodiments of the invention, the insert, held at the predefined location, does not contact tissue of the stoma.

According to some embodiments of the invention, the insert is located at a distal side of an ostomy cap.

According to some embodiments of the invention, the ostomy cap is provided to the user with the insert contained therein.

According to some embodiments of the invention, the predefined location is circumferential to the stoma.

According to some embodiments of the invention, the shape of the pad is annular.

According to an aspect of some embodiments of the present invention there is provided a restraint for a collapsed waste collection pouch of an ostomy appliance comprising: a body, held to the ostomy appliance by surface bonding; positioned to restrain the collapsed pouch from expanding under pressure from within the ostomy appliance to the volume which the unrestrained pouch is rated to contain; and having the strength of the surface bonding set so that it breaks when pressed by a pressure from within the ostomy appliance which exceeds a predetermined threshold.

According to some embodiments of the invention, the body ceases to restrain the pouch upon the breaking of the surface bonding.

According to some embodiments of the invention, the restraint is a sealing cover for the ostomy appliance which resists the escape of stomal gases as long as the surface bonding is intact.

According to some embodiments of the invention, regions of surface bonding break at one of at least different two pressure thresholds; one threshold being predetermined for each region; breaking at the lower threshold comprising a loss of resistance to the escape of stomal gasses; and breaking at the higher threshold comprising loss of restraint on the expansion of the pouch.

According to some embodiments of the invention, the surface bond is by welding.

According to some embodiments of the invention, the surface bond is by adhesion.

According to an aspect of some embodiments of the present invention there is provided a restraint for a collapsed waste collection pouch of an ostomy appliance, comprising: a body; upon the body, one element of at least one pair comprising a receiving aperture and an inserting projection, the projection sized to insert into the aperture and form a fitting attachment, the other element of the at least one pair being upon the ostomy appliance; such that the attached body is positioned to restrain the collapsed pouch from expanding under pressure from within the ostomy appliance to the volume which the unrestrained pouch is rated to contain; and the strength of the fitting attachment is set so that it breaks when pressed by a pressure from within the ostomy appliance which exceeds a predetermined threshold.

According to some embodiments of the invention, the restraint is fixedly attached to the ostomy appliance through a flexible member.

According to some embodiments of the invention, the flexible member is a hinge.

According to some embodiments of the invention, the elements of the at least one pair are disposed on facing surfaces of the body and the ostomy appliance.

According to some embodiments of the invention, at least one element of the at least one pair comprising a receiving aperture and inserting projection is of variable size, at least across a profile, such that the relative size of receiving aperture and projection at the place of attachment is selected by the relative positioning of the pair elements.

According to some embodiments of the invention, the attachment-breaking pressure is different depending on the relative attached positioning of the at least one pair comprising a receiving aperture and inserting projection.

According to some embodiments of the invention, at least two regions of fitting attachment have attachment broken, each above a different pressure threshold; one threshold being higher than the other; attachment loss at the lower threshold comprising a loss of resistance to the escape of stomal gasses from the ostomy appliance; and attachment loss at the higher threshold comprising loss of restraint on the expansion of the pouch.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
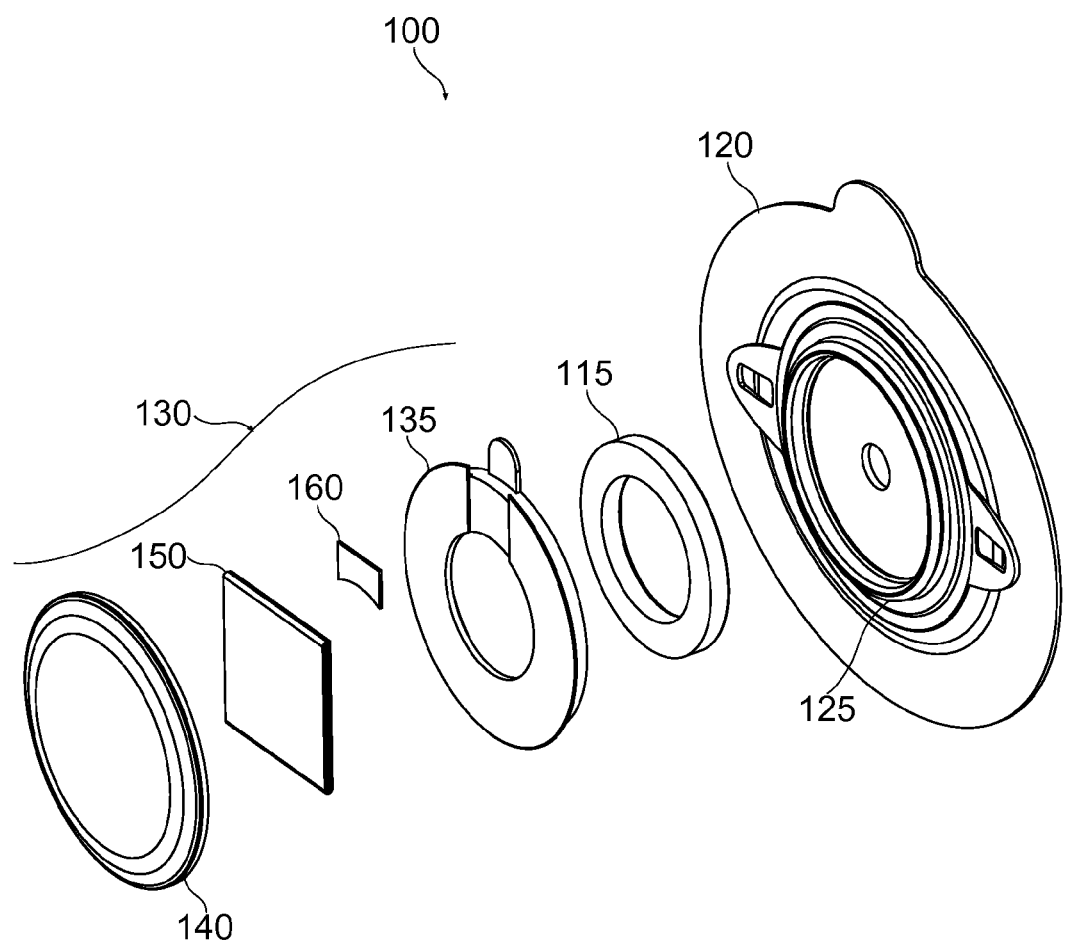
FIG. 1A schematically illustrates an exploded perspective view of an exemplary ostomy appliance, in accordance with some embodiments of the present invention.

The present invention, in some embodiments thereof, relates to the field of surgically created openings for stomal discharge removal (stoma) in living subjects, and more particularly, to devices and methods for covering a stoma as may be used in the case of a colostomy, ileostomy or urostomy.

Overview

An aspect of some embodiments of the present invention relates to ostomy appliances which are aesthetic, and/or aesthetically unobtrusive. A potential advantage of aesthetic improvement of an ostomy appliance is that it is thereby less noticeable and/or less objectionable to the appliance user and/or to persons around the appliance user.

An aspect of some embodiments of the present invention relates to the cleanliness of the ostomy appliance. A potential advantage of improved cleanliness is improved hygiene, and, as a consequence, improved user experience. A potential advantage of improved cleanliness is reduced tissue irritation and/or infection for a user. A potential advantage of improved cleanliness is a longer service life for ostomy components prone to absorbing noxious odors. A potential advantage of improved cleanliness is a longer service life for ostomy components prone to seal degradation.

An aspect of some embodiments of the present invention relates to ostomy appliances which are convenient to operate. In this aspect, convenience potentially comprises one or more of, for example: a reduced number of operating steps, a reduced number of separate components, features which assist users with sensory and/or motor impairments, and a reduced frequency of operating steps.

An aspect of some embodiments of the present invention relates to ostomy appliances which are flexible. A potential advantage of a flexible ostomy appliance is that it is more comfortable for a user to wear.

Fluid Introduction to the Stoma

An aspect of some embodiments of the invention relates to irrigation of the stoma, which introduces fluids within the stoma. This task is performed, for example, to introduce fluids into the intestine to initiate bowel evacuation. The directing of irrigating fluids is a potentially awkward task, especially for users with sensory and/or motor impairments.

An aspect of some embodiments of the invention relates to flushing of the stoma, which introduces fluids to outer and/or nearby regions of the stoma. This task is performed, for example, in order to clean outer and/or near-proximal surfaces of the stoma and portions of the ostomy appliance. Features disclosed herein which assist and/or improve stomal cleaning provide potential improvements to the wearing and/or use characteristics of a stomal appliance.

In some embodiments of the invention, a cap with a lumen sized and positioned for the directed delivery of fluids to the stoma is provided. In some embodiments, the user attaches the cap to the ostomy appliance especially for irrigation and/or flushing tasks, and detaches it afterward. In some embodiments, the cap is worn continuously, and includes additional cap features such as, for example, a pouch, filtering, and/or a pressure-sensitive pouch restraint. In some embodiments of the invention, the lumen is short, and fluid flushes the more external regions of the stoma. In some embodiments of the invention, the lumen is extended by a tubule adapted to insert into the stoma, and fluid irrigates the more internal regions of the stoma. Optionally, the cap is provided with an always open or closed proximal end, or with a removable cover.

A potential advantage of a cap with an integral irrigating and/or flushing lumen is to allow cleansing of the stoma, for example to dilute, loosen, and/or remove tissue-irritating contamination, which may then be removed in a waste collection pouch, without fully disassembling the ostomy appliance. Another potential advantage is to simplify cleaning of the stoma for the user, for example, by locking into place so that fluid is directed to the required portion of the stoma and recovered without leakage or spillage.

In some embodiments of the invention, an internal element of the ostomy appliance is a flushing element, provided with a flushing channel for receiving and conveying a cleaning fluid to one or more outlets around the stoma. In some embodiments of the invention, an external attachment structure is provided into which fluid is supplied, for example, by injection from a syringe. In some embodiments of the invention, channel outlets are distributed around the circumference of the internal element. In some embodiments of the invention, channel outlets are configured with one-way valves, for example flutter valves, such that materials including fluids can be injected under forward pressure, but are prevented from entering the channel outlets from within the appliance interior under reverse pressure.

In some embodiments of the invention, the flushing element also acts as a seal for the ostomy appliance. In some embodiments, the seal is against the leakage of stomal discharge to the outside of the ostomy appliance. In some embodiments, the seal is against the leakage of stomal discharge to peristomal skin covered by the ostomy appliance.

A potential advantage of a flushing element is to allow cleansing of the stoma, for example to dilute or remove tissue-irritating contamination buildup, without opening the ostomy apparatus. Another potential advantage is to allow more thorough cleaning of portions of the ostomy apparatus during use, potentially extending the practical wearing duration of components prone to contamination. Another potential advantage is to simplify cleaning of the stoma for the user. Another potential advantage is to allow the user to soften fecal material accumulating in the ostomy appliance, thus easing its flow into the collection bag. A potential advantage of valved outlets is to prevent the escape of stomal discharge and/or the blockage of the vents by stomal discharge.

An aspect of some embodiments of the invention relates to a cleansing device which assists in removing contamination from exterior portions of the stoma during operations related to the management of stomal discharge. Wiping of stomal regions is a potentially awkward task, especially for users with sensory and/or motor impairments.

In some embodiments of the invention, the cleansing device is provided with a portion carrying a cleaning material, and a portion for handling the device. In some embodiments, the cleansing device is adapted to be inserted into the lumen of an open ostomy appliance, and maneuvered such that the cleaning material wipes over accessible portions of the stoma, cleaning them. In some embodiments of the invention, the cleaning material is replaceable. In some embodiments of the invention, the entire cleansing device is disposable. In some embodiments of the invention, disposable parts of the cleansing device are made of materials which degrade in a manner compatible with the requirements of standard sewage systems.

A potential advantage of the cleansing device is the use of the surfaces of the ostomy appliance to guide cleansing material to the region to be cleaned without a requirement for visual feedback and/or fine motor coordination. Another potential advantage of the cleansing device is to create separation between hand and stoma during cleaning, to potentially reduce hand contamination by stomal discharge.

Waste Outflow Restriction

An aspect of some embodiments of the invention relates to a stomal plug which restricts the outflow of stomal discharge from the stoma into the interior of the ostomy appliance. Even with a sealed stomal covering in place, preventing and/or quickly absorbing continuous stomal discharge outflow from the stoma potentially reduces undesired effects of stomal discharge contact on external tissue and/or components of the ostomy appliance.

In some embodiments of the invention, a plug is provided which inserts into the stoma opening, providing an at least partial seal against the outflow of stomal discharge to the interior of the ostomy appliance. In some embodiments, the plug is formed of a material capable of absorbing at least a portion of the stomal discharge; for example, stomal discharge bypassing a partial seal formed by the plug. Potentially, absorption is useful for controlling the discharge of liquid and/or mucosal discharges which have the greatest tendency to find their way to sensitive and/or difficult-to-clean regions within the interior of the ostomy appliance. In some embodiments, the plug expands upon absorption of stomal discharge, which potentially improves its sealing capability. In some embodiments, the plug is permeable to gas. In some embodiments, the plug comprises a material, for example activated carbon, which deodorizes gas flowing through it; for example by filtering. In some embodiments, the plug exerts force on the wall of the stoma which is in the range of, for example: 10-30 mmHg, 80-100 mmHg, 60-200 mmHg, or another range which reaches higher and/or lower pressures. In some embodiments, the plug is relatively soft, for example, in the range of 20-50 Shore A. Potentially, a soft plug comprises a lowered risk of injury to the surrounding tissue during extended wear.

In some embodiments, the plug is attached to another component of the ostomy appliance, for example, to a portion of the collection pouch. In some embodiments, the plug exits the stoma upon deployment of the collection pouch, for example, by being pulled away from the stoma by a portion of pouch to which is it attached. In some embodiments, the plug is pulled and/or pushed into the collection pouch upon pouch deployment.

In some embodiments of the invention, a stomal balloon plug is provided which inserts into the stoma opening. In some embodiments, the balloon plug inserts into the stoma opening in an at least partially deflated state, and is then inflated, providing an at least partial seal against stomal discharge reaching the interior of the ostomy appliance. In some embodiments, the plug is provided with a valved tube in communication with the exterior of the ostomy appliance, through which inflation fluid, for example, air and/or saline, is pumped or released in order to inflate or deflate the plug. In some embodiments, the plug is attached to a portion of the ostomy appliance, for example, to a portion of the collection pouch. In some embodiments, the attachment exerts a proximal-acting force on the stomal balloon plug. This provides the potential advantage of helping to secure the sealing of the plug. In some embodiments, the balloon is deflated before removal from the stoma. In some embodiments, the plug exits the stoma upon deployment of the collection pouch, for example, by being pulled away from the stoma by a portion of pouch to which is it attached. In some embodiments, the plug is pulled into the collection pouch upon deployment. In some embodiments, the balloon plug is sufficiently deformable when inflated that it is kept inflated externally, and inserted into the stoma opening and removed without special inflation and/or deflation steps.

A potential advantage of the stomal plug is to reduce the amount of external tissue irritation caused by stomal discharge entering the interior of the ostomy appliance. Another potential advantage of the stomal plug is to reduce contamination of other parts of the ostomy appliance. Reduced contamination in turn potentially allows appliance components to remain in service longer before cleaning or replacement is necessary. Another potential advantage of the stomal plug is reduced risk of leakage out of the appliance. A potential advantage of attaching the stomal plug to a portion of the ostomy device is prevention of the plug from falling into the stoma. A potential advantage of pulling the stomal plug into the collection pouch upon deployment is the simplification of stomal discharge management operations for the user.

Pouch Restraints

An aspect of some embodiments of the invention relates to a restraint controlling the deployment of the stomal discharge collection pouch. More particularly, the invention relates to mechanisms of attachment and pressure sensing.

In some embodiments of the invention, a mechanism of pressure sensing for determining automatic restraint release is implemented in the attachment mechanism of the restraint cover of the ostomy device.

In some exemplary embodiments of the present invention, a cover attaches to an ostomy appliance by one or more pressure-fitting projections (in the form, for example, of a bead), on a surface facing the ostomy apparatus. Such a projection inserts into a corresponding mating depression on a surface of the ostomy apparatus. In some embodiments, under sufficient outward pressure acting on the body of the cover, attachment is broken to permit pouch deployment. In some embodiments, the pressure is communicated by pressing from the pouch itself. In some embodiments, the pressure is communicated by the pressure of gas contained by the ostomy appliance but released from containment by the pouch, for example, through an internal filter. Optionally, pairs and/or regions of bead and mating depressions are provided with different attachment strengths, such that exceeding a lower pressure threshold breaks a seal against the release of gas, and exceeding a higher pressure threshold releases restraint on pouch deployment. Optionally, one or both of bead and mating depression (or a plurality thereof) are constructed such that the relative rotational angle at which they mate determines the release pressure, for example, by variations in width. Optionally, the release pressure is at least partially determined by a degree of deformation introduced to the body of the cover, such that a change in relative angle of contact is a determining factor in triggering release. Optionally, the faces on which bead and mating depression occur are reversed or mixed.

The bead-and-depression pressure sensing/attachment mechanism is potentially advantageous in ostomy appliances designed to flex; for example, where shape changes due to flexing do not dislodge the bead, but might dislodge a wrap-around attachment design. The mechanism potentially requires less fine motor control to seal and/or re-seal in case of partial opening. A user-selectable release pressure is potentially useful for setting the pressure release characteristics of the cover, according to the preferences of the user. Staged pressure-release characteristics provide a potential benefit for allowing control of gas release independently of the deployment of a pouch for receiving non-gaseous stomal discharge.

In some exemplary embodiments of the invention, a cover is integrally attached to an ostomy appliance component by a hinge element. Potentially, one or more securing elements, such as a hook-and-flange or a snap, serve to hold an attached cover closed. In some embodiments of the invention, the securing element is configured to release upon sufficient pressure occurring behind the cover. Optionally, another closure structure, for example the bead-and-channel mechanism, is used.

A hinged cover is potentially easier to handle and operate by a user than a freely detachable cover. Another potential advantage of a hinged cover is reduced production expense, as a single part can provide the functions of both housing and cover.

Additionally or alternatively, in some embodiments of the invention, a cover is attached to an ostomy appliance component by pressure-breaking attachments formed at regions of contact between appliance and cover, by mechanisms such as adhesive, or break-away welding. Additionally or alternatively, a surface of a collapsed pouch is attached to an ostomy appliance component by pressure-breaking attachments, thereby preventing said collapsed pouch from deploying.

A potential advantage of a pressure-breaking attachment mechanism is the ability to provide a pre-packaged pouch module which requires fewer user steps to operate. Another potential advantage of a pressure-breaking attachment mechanism is more reproducible manufacturing, resulting in reduced variability of release pressure.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Ostomy Appliance

Figure 1B:
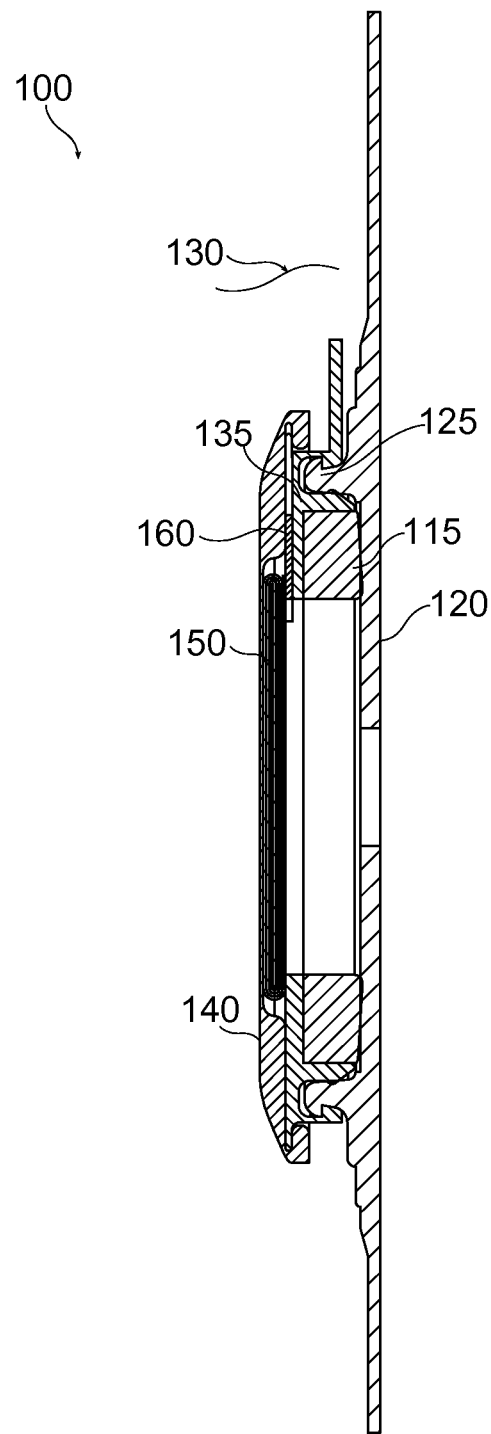
FIG. 1B schematically illustrates a sectional view of the exemplary ostomy appliance of FIG. 1A, in accordance with some embodiments of the present invention.

Reference is now made to FIG. 1A, which schematically illustrates an exploded perspective view of an ostomy appliance 100, and FIG. 1B, which schematically illustrates a sectional view of the ostomy appliance 100 of FIG. 1A, according to some exemplary embodiments of the present invention.

In some embodiments of the invention, the ostomy appliance 100 comprises a stack of ostomy components, exemplary embodiments of which are described in overview. Most distal, and worn against the skin of the user (not shown), is the ostomy wafer, 120. Exemplary ostomy cap 130 is attached to ostomy wafer 120, for example, via flange 125. In some embodiments, a sealing element 115 is positioned between the ostomy cap 130 and the ostomy wafer 120. In some embodiments, the ostomy cap 130 comprises a housing 135 with a central annulus. In some embodiments, housing 135 has a cover 140. In some embodiments, a collapsed stomal discharge collection pouch 150 is contained within and/or next to the annulus of housing 135. In some embodiments, the housing 135 contains a gas filter 160 for filtering gasses flowing from the stoma. Wafer 120, sealing element 115, and cap housing 135 have apertures through which stomal discharge passes into collapsed pouch 150 for disposal.

In an exemplary embodiment of the invention, cover 140 is a restraint on the deployment of pouch 150 until it is removed, for example manually, or in response to pressure. As shown in FIG. 1A, exemplary cover 140 is the most proximal element of the stack of ostomy components.

A function of sealing element 115 in some embodiments is to provide auxiliary sealing, which, for example, potentially helps prevent the contact of stomal discharge with skin, and/or helps prevent leakage through the attachment interface of cap 130 with wafer 120. A function of sealing element 115 in some embodiments is to occupy at least a portion of the space between the stoma and housing 135 so as to limit the accumulation of fecal material therebetween.

A function of optional gas filter 160 in some embodiments is to permit the gradual outflow of stomal gasses, potentially preventing the build-up of internal pressure. In some embodiments, gas filter 160 comprises of an absorbing material, such as activated carbon, or another odor-neutralizing material, which filters noxious odors from outflowing gasses.

Not all ostomy components shown are used in all embodiments of the ostomy appliance invention. A generic ostomy appliance may be described simply as a base component, such as ostomy wafer, having an annular projection large enough to contain the stoma, and a closure on the proximal end.

In an exemplary embodiment of the invention, an ostomy adaptor (not shown), is present, which serves the function of connecting the ostomy cap 130 to the ostomy wafer 120, and/or additional functions according to specifics of the embodiment. Other embodiments of ostomy appliances usable with one or more features and combinations thereof as described herein are set forth, for example, by International Patent Application No. PCT/IB2011/051933, International Patent Application No. PCT/IB2011/051938, International Patent Application No. PCT/IB2011/051932, International Patent Application No. PCT/IL2010/00056 and International Patent Application No. PCT/IL2013/050401.

Cleaning of a Stomal Appliance

Flushing-Type Sealing Element with Internal Fluid Distribution

Figure 3A:
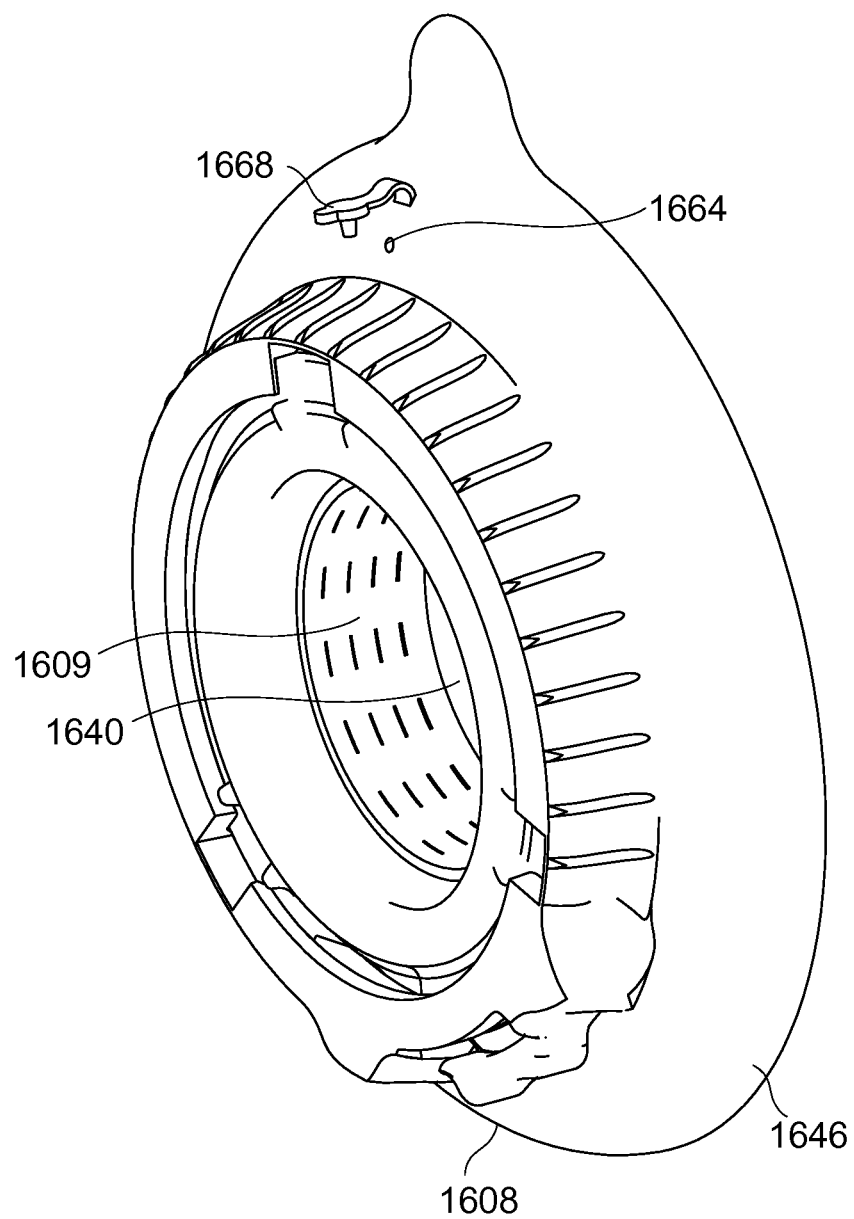
FIG. 3A schematically illustrates a perspective view of an adaptor having a flushing-type sealing element in an ostomy appliance.
Figure 3B:
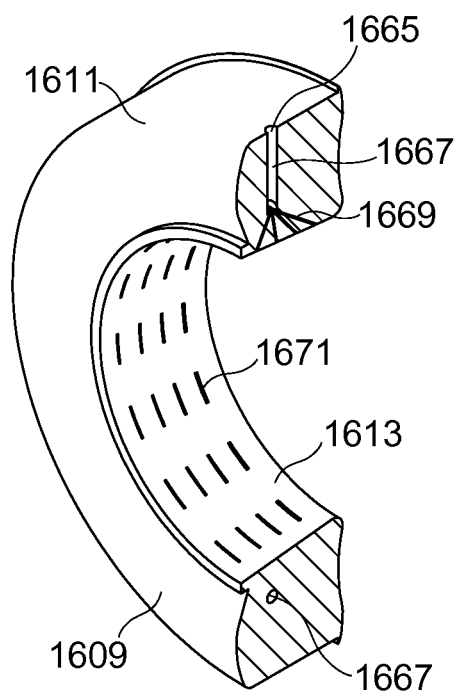
FIG. 3B schematically illustrates a perspective view of a cross-section of a sealing element for use with the adaptor of FIG. 3A, in accordance with some exemplary embodiments of the present invention.
Figure 3C:
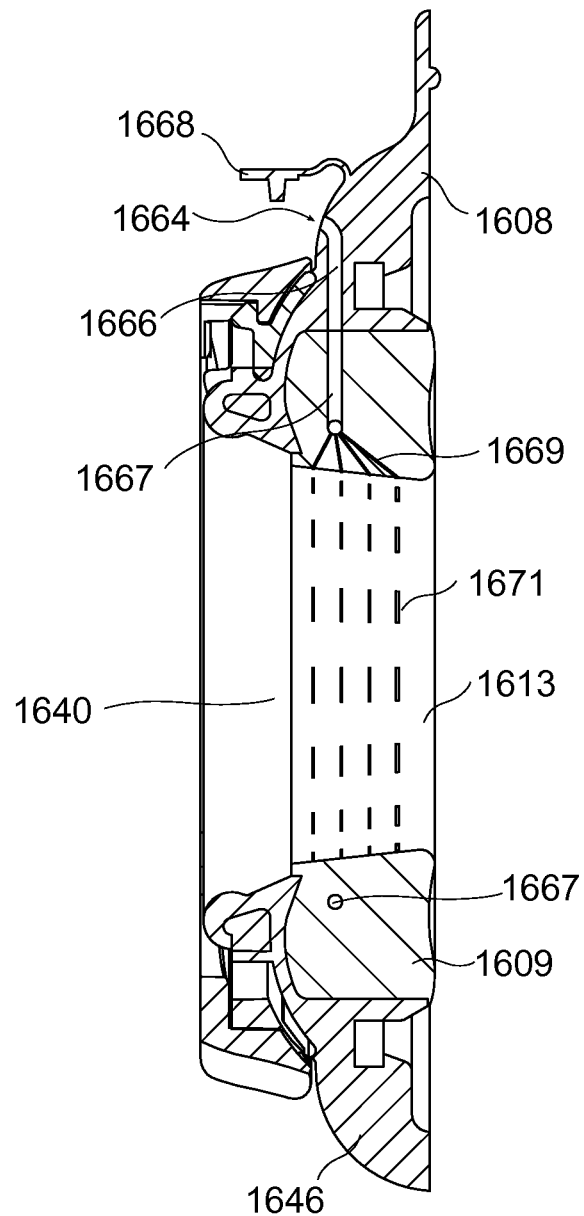
FIG. 3C schematically illustrates a sectional view of the adaptor of FIG. 3A with the sealing element of FIG. 3B, in accordance with some exemplary embodiments of the present invention.

Reference is now made to FIGS. 3A and 3B which schematically illustrate perspective views of an ostomy appliance adaptor 1608 having a flushing-type sealing element 1609, and to FIG. 3C which schematically illustrates a sectional view of the adaptor with the sealing element, according to some exemplary embodiments of the present invention.

Some potential advantages of flushing element 1609 relate to issues of stoma cleanliness. Stomal discharge residue potentially causes irritation and/or inflammation of external tissue that it contacts. Stomal discharge residue is potentially unpleasant for the user, for example due to odor and/or appearance. Potentially, residue odors are acquired over time through absorption by components in regular contact with stomal discharge.

Adaptor 1608 including sealing element 1609 is adapted to introduce fluid into an internal portion of adaptor 1608. Optionally, sealing element 1609 may be made of a soft elastomer, for example silicon rubber, or a thermoplastic elastomer, for example SEBS. The durometer of sealing element 1609 is, for example, between 5-20 Shore A. Optionally, said fluid can be introduced into the stoma (not shown), for example for intestinal irrigation. According to one or more of the embodiments, the fluid lubricates and/or loosens the flow of stomal discharge through adaptor 1608 into the pouch, washes the stoma, washes the peristomal skin, washes the interior of the adaptor and/or irrigates an interior of the intestine. Optionally, flushing is performed without sealing element 1609 by introducing the flushing fluid into cavity 1640.

In some exemplary embodiments, adaptor body 1646 includes a flushing port 1664 through which the flushing fluid is injected, or otherwise administered, into adaptor 1608. In an exemplary embodiment of the invention, a flushing lumen 1666 extends from flushing port 1664 through adaptor body 1646 to cavity 1640, connecting to a feeder port 1665 in an outer wall 1611 of sealing element 1609. A feeder lumen 1667 inside sealing element 1609 extends from feeder port 1665 to one or more distribution lumens 1669, for example four distribution lumens, peripherally extending along at least a portion of the sealing element. One or more flushing openings 1671, for example, 4, 8, 16, or 64 openings, are spaced along an inner wall 1613 of sealing element 1609 and fluid connect to distribution lumens 1669. Optionally, the number of distribution lumens 1669 and/or number of flushing openings 1671 included in sealing element 1609 varies with a particular flushing application. Optionally, a design including the location, size, and/or shape of distribution lumens 1669 and/or flushing openings 1671 in sealing element 1609 varies with the application. For example, a sealing element used only for irrigation of the stoma may differ from a sealing element used for flushing the interior of the adaptor and/or washing the stoma and/or the peristomal skin, by the location of the outlets which direct washing fluids. Examples of outlets provided to irrigate the stoma include outlets which terminate near and/or are directed into the stomal mouth, and outlets that comprise one or more tubules extending from the sealing element into the stoma. And example of outlets provided to flush the exterior of the stoma includes outlets arranged around and/or direct toward exterior stomal tissue. An example of outlets provided to help clean the interior of the ostomy appliance include outlets directed toward the appliance walls. As another example, outlets may be located near the top of the ostomy appliance, providing the potential advantage of washing contaminants down with the flow of gravity.

An exemplary method of performing flushing, according to some embodiments, includes the user introducing the flushing fluid through flushing port 1664 into flushing lumen 1666. Optionally, a volume of the flushing fluid ranges from 20 ml-1000 ml, or more, for example, 50 ml, 80 ml, 150 ml, 250 ml, 350 ml, 500 ml, 700 ml, 850 ml, 950 ml, 1100 ml, 1200 ml, 1500 ml. Fluid flow through flushing lumen 1666 enters through feeder port 1665 into feeder lumen 1667, and therefrom into distribution lumens 1669. The flushing fluid flowing through distribution lumens 1669 exits through flushing openings 1671 and flows therefrom into cavity 1640 and other areas to be flushed. In some exemplary embodiments, sealing element 1609 includes a slot peripherally extending along outer wall 1611. This provides the potential advantage of allowing the slot, whatever its rotational position inside cavity 1640, to always be aligned at some location with flushing lumen 1666 so that the flushing fluid flowing through the flushing lumen enters into the slot.

In some embodiments, extending from the slot are one or more feeder lumens 1667, for example 2, 4, 7, 10, or more feeder lumens, which fluidly connect with one or more distribution lumens 1669 and into which the flushing fluid from the slot flows. In some exemplary embodiments, distribution lumens 1669 and flushing openings 1671 are adapted in sealing element 1609 to obtain fluid flow in a predetermined location and/or direction. Flow is directed, for example, to the stoma interior, the stoma exterior, and or surfaces of the ostomy appliance interior. In some embodiments, flushing openings 1671 are sized to allow fluid flow out the openings under pressure, but small enough to substantially prevent fluid under a lower pressure from flowing back into the openings. In this manner, flushing openings 1671 act as one-way valves, or flutter valves, and prevent outflow of stomal discharge through the flushing system. In some embodiments, Optionally, fluid flow out of flushing openings 1671 is at a pressure of up to 300 mm/Hg, for example 100 mm/Hg, 150 mm/Hg, 200 mm/Hg, or 250 mm/Hg. The fluid is pressurized, for example, by the use of a syringe, or by being in fluid communication with an elevated reservoir, such as a bag. In some exemplary embodiments, flushing port 1664 is closed by a flushing plug 1668. Flushing plug 1668 prevents outflow of flushing fluid administered into adaptor 1608. Optionally, flushing plug 1668 prevents outflow of gases and/or stomal discharge from within adaptor 1608 through the flushing system. In some embodiments, a one-way valve (not shown) is included in flushing lumen 1666.

It should be noted that the sealing and flushing functions, though related, are potentially independent. In some embodiments, a flushing element operating as described is, for example, not sized to perform sealing, or is made of a material which is insufficiently elastic to form a sealing interface.

Exemplary Flushing Sealing Element with External Fluid Distribution

Figure 4A:
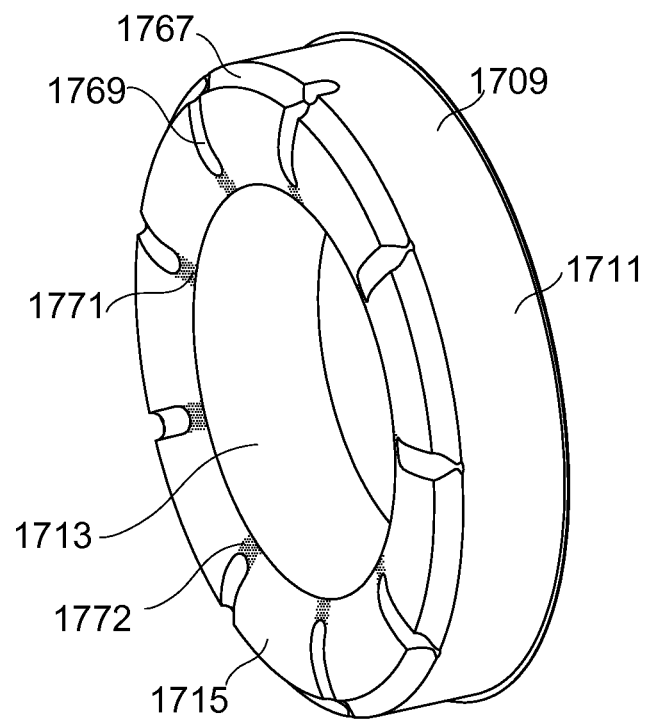
FIG. 4A schematically illustrates a perspective view of a flushing-type sealing element, in accordance with some exemplary embodiments of the present invention.
Figure 4B:
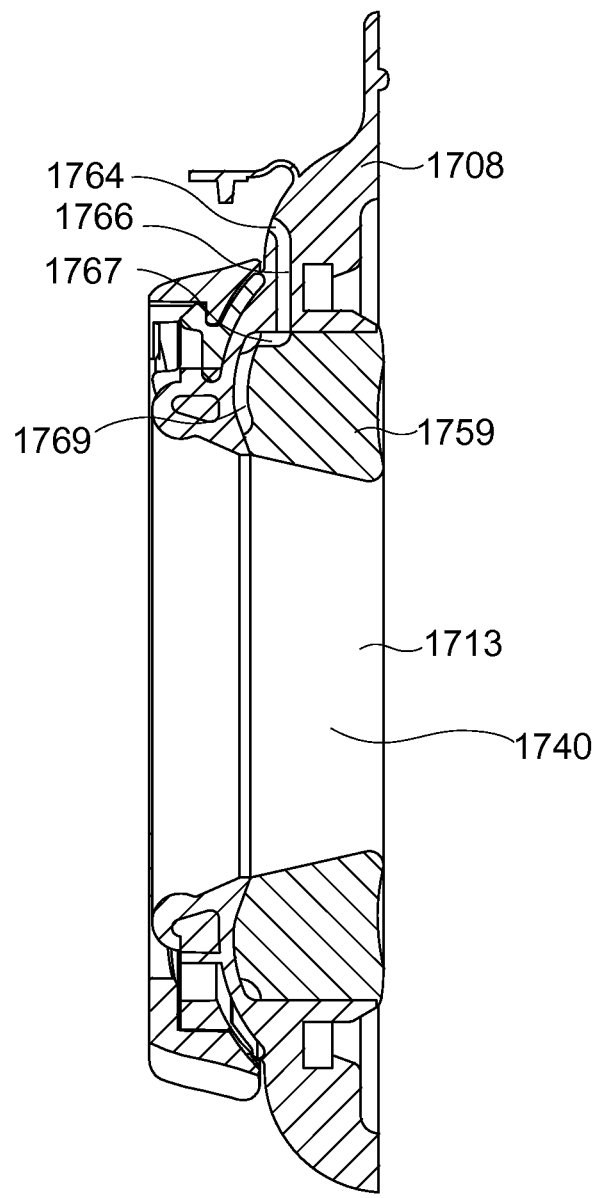
FIG. 4B schematically illustrates a sectional view of an adaptor with the sealing element of FIG. 4A inside a cavity, in accordance with some exemplary embodiments of the present invention.

Reference is now made to FIG. 4A which schematically illustrates a perspective view of a flushing-type sealing element 1709, and to FIG. 4B which schematically illustrates a sectional view of adaptor 1708 with sealing element 1709 inside cavity 1740, according to some exemplary embodiments of the present invention.

In some exemplary embodiments, sealing element 1709 includes a feeder channel 1767 circumferentially extending along outer wall 1711 and connecting to one or more inlet slots 1769. Inlet slots 1769 extend from feeder channel 1767 along a proximal side 1715 of sealing element 1709 in a direction towards an inner wall 1713 and terminate at flushing openings 1771 proximal to inner wall 1713. In some embodiments, flushing openings 1771 include reduced-size slots which allow fluid flow in a direction into cavity 1740 while preventing backflow up into inlet slots 1769 (optionally functionally similar to a flutter valve). Optionally, sealing element 1609 may be made of a soft elastomer, for example silicon rubber, or a thermoplastic elastomer, for example SEBS.

An exemplary method of performing flushing, according to some embodiments, includes the user introducing the flushing fluid through flushing port 1764 into flushing lumen 1766. Fluid flow through flushing lumen 1766 enters into feeder slot 1767 and therefrom into inlet slot 1769. The flushing fluid flowing through inlet slots 1769 exit through flushing openings 1771 and flow therefrom into cavity 1740 and other areas to be flushed.

In some exemplary embodiments, openings 1771 are located on inner wall 1713. In some embodiments, gaps 1772 are left between openings 1771 and inner wall 1713, such that inlet slots 1769 are normally not in fluid communication with cavity 1740. A potential advantage of such gaps is to restrict backflow of gases or discharge matter from cavity 1740 into slots 1769 while inflow of flushing fluid from slots 1769 into cavity 1740 is possible, through a check-valve mechanism known in the art as a "flutter valve" or a "duckbill valve". When a pressurized fluid is present in inlet slots 1769, its pressure acts on gaps 1772 and forces them to shift in the distal direction thus enabling the fluid to flow into cavity 1740. When a pressurized fluid is present in cavity 1740, its pressure acts on inner wall 1713. As a result gaps 1772 are tightened onto the body of the adaptor, restricting flow of fluid from cavity 1740 into inlet slots 1769. Optionally, flow is directed, for example, to the stoma interior, the stoma exterior, and or surfaces of the ostomy appliance interior. Flow direction is determined, for example, by the angle of the face from which the fluid exits, and the angle of the lumen before reaching the fluid outlet. In some embodiments, the aperture shape is long in one direction, and/or the shape of the approach lumen is fan-like, so as to potentially impart to exiting water a fan-like dispersal pattern. In some embodiments, a more circular outlet potentially provides a more concentrated jet of fluid.

Exemplary Flushing-Type Sealing Element with Flushing Tube

Figure 5:
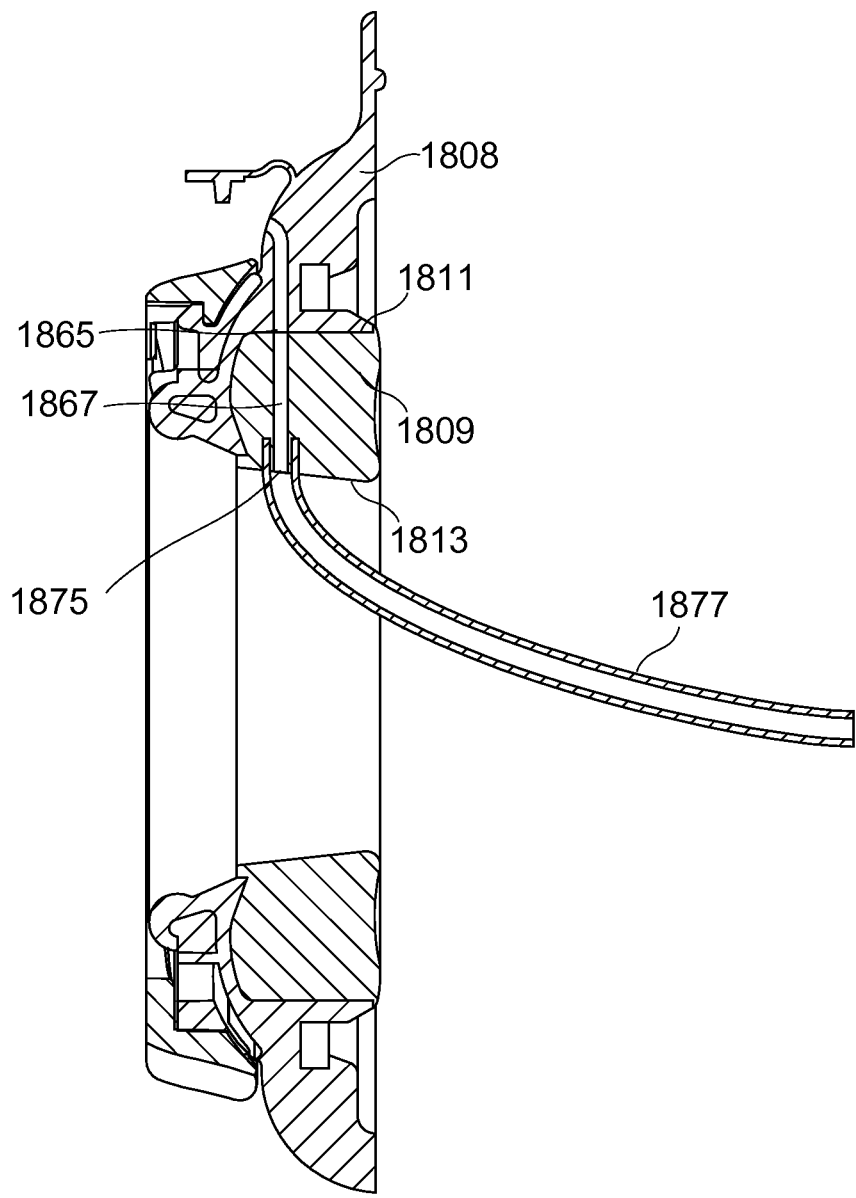
FIG. 5 schematically illustrates a sectional view of an adaptor including a flushing-type sealing element in an ostomy appliance with an extension tubule, in accordance with some exemplary embodiments of the present invention.

Reference is now made to FIG. 5 which schematically illustrates a sectional view of adaptor 1808 including a flushing-type sealing element 1809 for use with an ostomy appliance, according to some exemplary embodiments of the present invention.

In some embodiments, sealing element 1809 includes a feeder lumen 1867 extending from an outer wall 1811 to an inner wall 1813 in the sealing element, having a feeder port 1865 on the outer wall, and an outlet port 1875 on the inner wall. In some embodiments, outlet port 1875 is adapted to receive a flushing tube 1877 for insertion into the stoma (not shown) for intestinal flushing or irrigation.

Figure 2A:
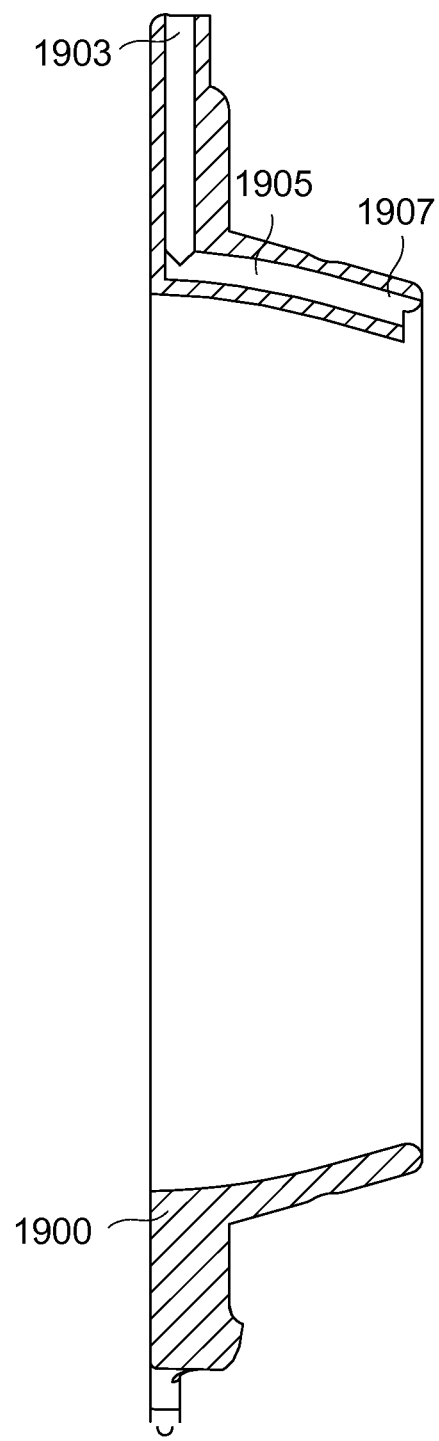
FIG. 2A schematically illustrates a sectional view of an exemplary irrigating ostomy cap, in accordance with some embodiments of the present invention.
Figure 2B:
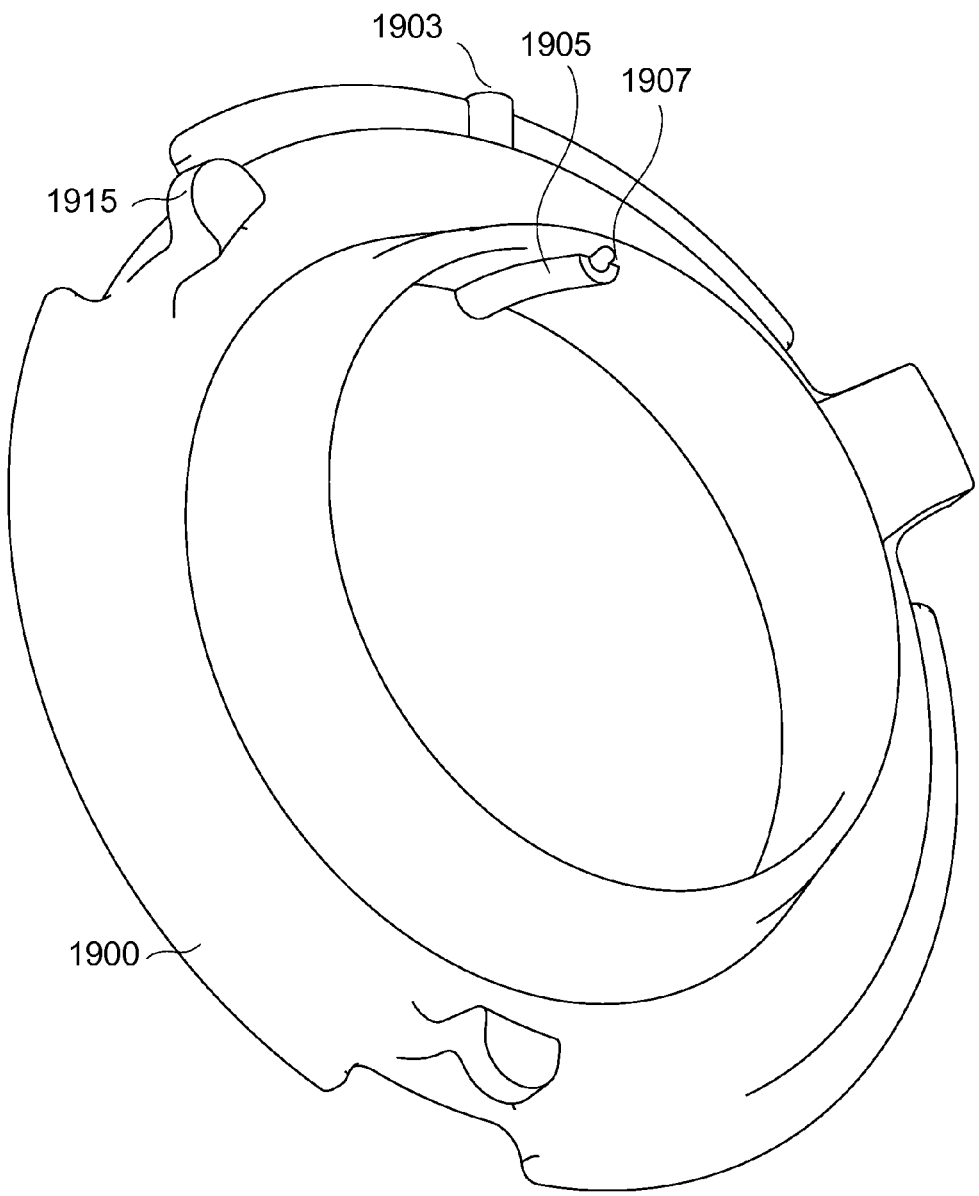
FIG. 2B schematically illustrates a perspective view of an exemplary irrigating ostomy cap, in accordance with some embodiments of the present invention.
Figure 2C:
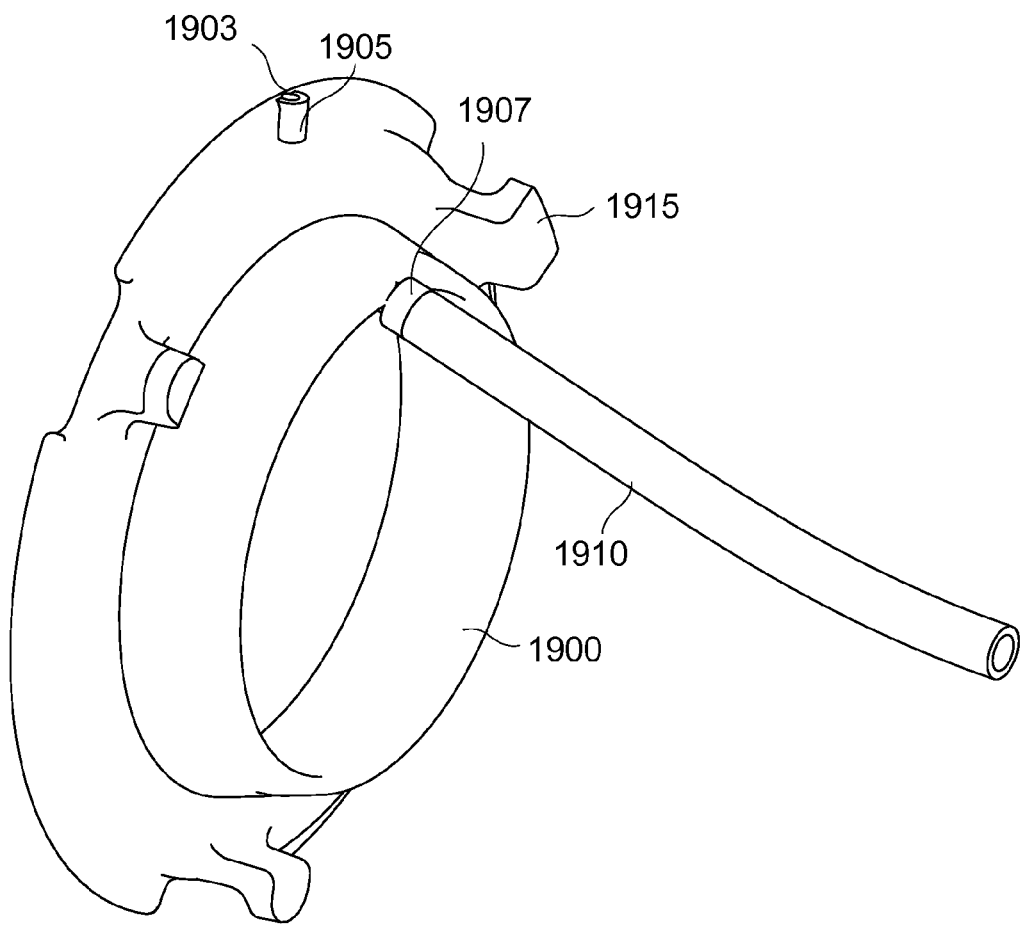
FIG. 2C schematically illustrates a perspective view of an exemplary irrigating ostomy cap with an extension tubule, in accordance with some embodiments of the present invention.

Reference is now made to FIG. 2A which schematically illustrates a sectional view of an exemplary irrigating ostomy cap 1900, FIG. 2B which schematically illustrates a perspective view of irrigating ostomy cap 1900, and FIG. 2C which schematically illustrates a perspective view of irrigating ostomy cap 1900 with an extension tubule 1910.

In some embodiments of the invention, irrigating ostomy cap 1900 has a lumen 1905, adapted at a proximal end 1903 to receive irrigating fluid, and at a distal end 1907, to deliver the fluid to a region of a stoma. Optionally, proximal end 1903 is sized and shaped so that it can be fitted to a syringe and/or tube in communication with a reservoir of irrigating fluid. In some embodiments, cap 1900 is adapted to insert within the lumen of an ostomy appliance (not shown). Optionally, cap 1900 is provided with an attachment mechanism, for example flange attachments 1915, suitable to the ostomy appliance. Optionally, distal end 1907 terminates exterior to the stoma when cap 1900 is attached. Optionally, an extension tube 1910 connects to distal end 1907 and extends it. Optionally, extension tube 1910 is adapted to be inserted into a stoma, to deliver irrigating fluids internally.

In some embodiments of the invention, irrigating cap 1900 includes one or more other ostomy cap features, including a collapsed pouch for receiving stomal discharge, a releasable pouch restraint, a pressure-release mechanism for pouch deployment, a filter for releasing stomal gasses, a mechanism for manually bleeding off stomal gasses, and/or other features associated with a cap disclosed herein. In some embodiments, irrigating cap 1900 includes other ostomy cap features known in the art.

A potential advantage of irrigating cap 1900 is to minimize the risk of spilling in the delivery of flushing fluids to the stoma. Another potential advantage is more reliable delivery of flushing fluids to one or more predetermined locations, according to the specific design of cap, lumen, and/or ostomy appliance. Optionally, said predetermined locations are difficult to access for cleaning, for example crevices of the appliance, or tissue locations prone to irritation by stomal discharge, for example peristomal skin. A potential advantage of cleaning with a cap 1900 designed for use with an installed ostomy appliance is a longer period of safe continuous wear.

Exemplary Ostomy Appliance Cleaning Device

Figure 6:
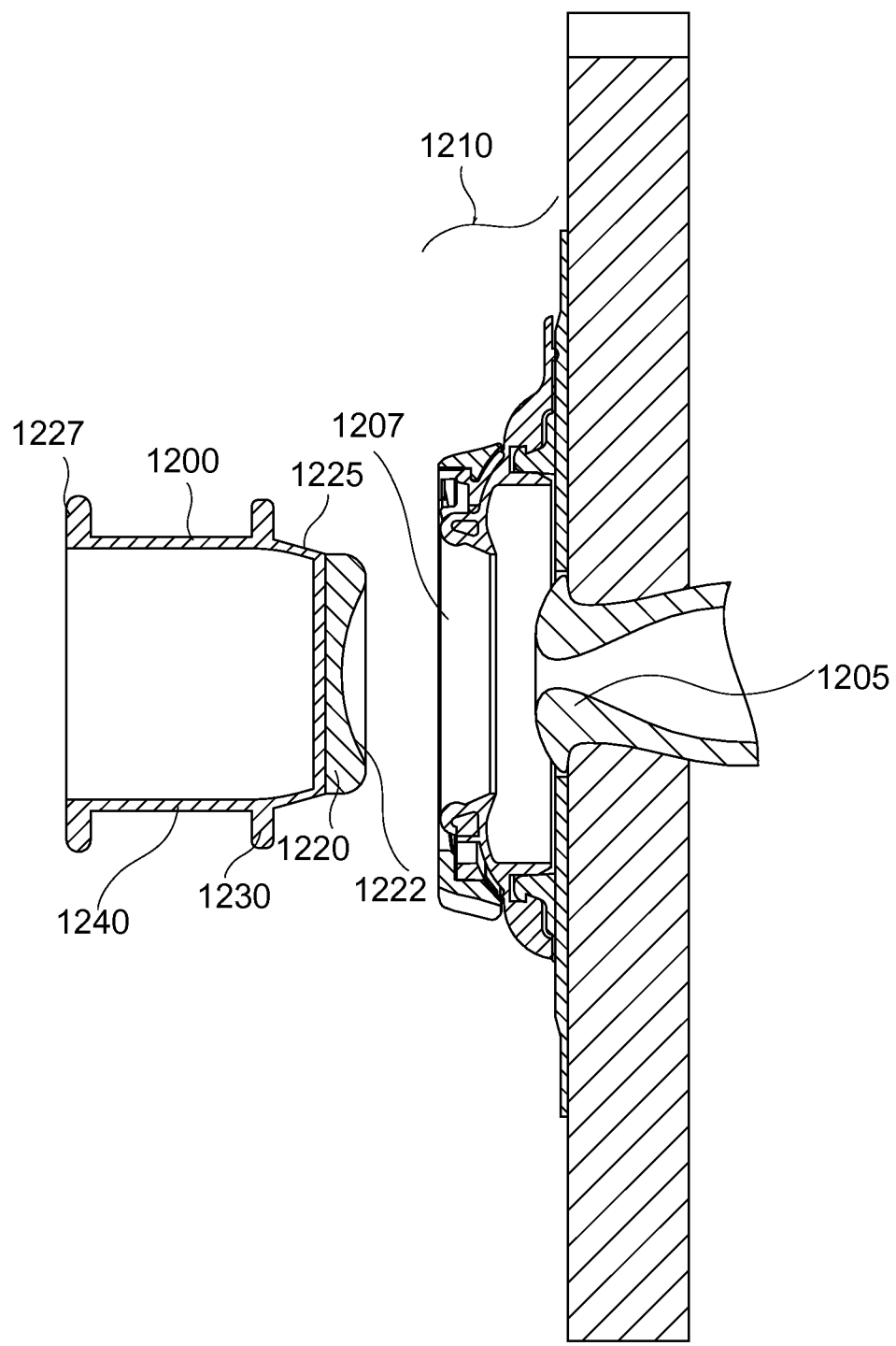
FIG. 6 schematically illustrates a sectional view of an exemplary ostomy cleaning cap in an approach position to an ostomy appliance attached over a stoma.

Reference is now made to FIG. 6 which schematically illustrates a sectional view of an exemplary ostomy cleaning device 1200 in an approach position to ostomy appliance 1210, attached over a stoma 1205, in accordance with an exemplary embodiment of the invention.

In some embodiments of the invention, cap 1200 comprises a grip 1240 located at its proximal end 1227. In some embodiments, cap 1200 comprises a cleansing element 1220 attached to its distal end 1225. The cleansing element is, for example, an absorbing pad, a cloth, foam, or cotton wool. Optionally, cleansing element 1220 comprises a cleansing agent, which is, for example, water, soap and/or alcohol. Optionally, the distal face 1222 of cleansing element 1220 is concave. A potential advantage of a concave distal face is conformation to the shape of the stoma.

In some embodiments, distal end 1225 is tapered. Potentially, the narrow end allows cleansing element 1220 to more easily enter the ostomy appliance lumen 1207. In some embodiments, the widening body guides the cleansing element 1220 toward the center of the ostomy appliance lumen 1207 on closer approach, through contacts with one or more surfaces of the appliance 1210. For example, a chamfered surface potentially pushes the cleaning device more toward the center of the ostomy appliance lumen 1207 as the device is pushed distally. In some embodiments, cap 1200 comprises a rim 1230 having an outer diameter larger than a portion of the opening to lumen 1207, obstructing deep entry of cap 1200 into lumen 1207.

A possible advantage of tapered distal end 1225 is to assist unobserved guidance of the cleansing element 1220 to regions to be cleaned. A possible advantage of obstructing rim 1230 is prevention of injury due to unintended penetration to the stoma.

A possible method of using cap 1200 is for the user to hold it by the grip 1240, and push it into lumen 1207 until cleansing element 1200 touches the stoma 1205. The user then wipes the stoma 1205 and surroundings. When done, the user removes cleansing cap 1200, and can close the ostomy apparatus for further wear.

In some embodiments, cap 1200 is at least partially comprised of materials compatible with sewage sanitation systems, so that soiled material can be more easily disposed of. The material may be, for example, loosely compressed paper fibers which disintegrate in water.

Preventative Stomal Cleaning

Exemplary Absorbing Pad Sealing Element

Figure 7:
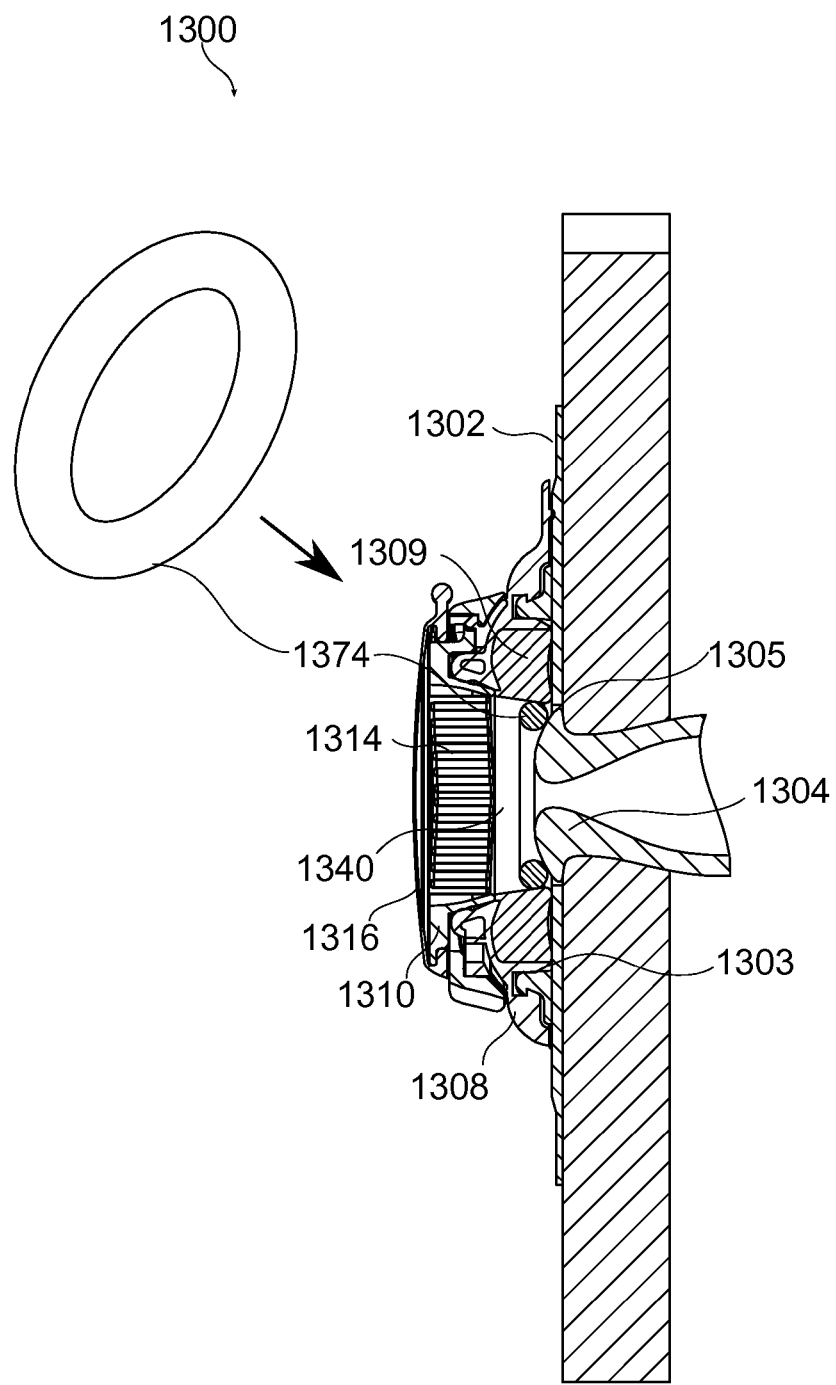
FIG. 7 schematically illustrates a sectional view of an exemplary ostomy appliance attached to a wafer covering the stoma and having an adaptor with an absorbing pad, in accordance with some embodiments of the present invention.

Reference is now made to FIG. 7 which schematically illustrates a sectional view of ostomy appliance 1300 attached to wafer 1302 covering stoma 1304 and having adaptor 1308 with an absorbing pad 1374, according to some embodiments of the present invention.

It is in general a potential advantage to reduce and/or postpone the flow of waste into the ostomy appliance itself, and particularly to sensitive tissue and/or appliance surfaces which are not replaced frequently. In some embodiments, absorbing pad 1374 is fitted inside cavity 1340 between stoma 1304 and pouch 1314, and is adapted to absorb liquid stomal discharge. Potentially, this reduces the effects of possible leakage of liquid stomal discharge from adaptor 1308, for example irritation or injury of peristomal tissue, odor and/or odor buildup, and waste contamination of difficult to clean areas. Potentially, solid discharge into cavity 1340 is also reduced by partial blockage. Optionally, absorbing pad 1374 peripherally surrounds stoma 1304. In some embodiments, an amount of liquid discharge absorbable by absorbing pad 1374 is up to 100 ml, for example, 1 ml, 5 ml, 10 ml, 20 ml, 35 ml, 45 ml, 50 ml, 60 ml, 75 ml, 85 ml, 90 ml, 95 ml. Optionally, absorbing pad 1374 absorbs amounts of liquid discharge in excess of 100 ml, for example, 120 ml, 150 ml, 180 ml, 200 ml, or more. In some embodiments, liquid stomal discharge absorption by absorbing pad 1374 reduces the sealing requirements of sealing element 1309 and/or at wafer/adaptor interface 1303. Additionally or alternatively, absorbing pad 1374 reduces an amount of liquid discharge required to be handled at wafer/stoma interface 1305 and/or wafer/adaptor interface 1303. In some embodiments, liquid discharge absorption by absorbing pad 1374 potentially facilitates cleaning of adaptor 1308 by preventing the discharge from reaching and/or accumulating on surfaces to be cleaned.

In some exemplary embodiments, absorbing pad 1374 is a disposable pad which is disposed of together with pouch 1314. Optionally, absorbing pad 1374 is pushed into pouch 1314 by the pressure of the stomal discharge flowing into the pouch. Optionally, absorbing pad 1374 is attached to cap 1310 so that removal of the cap or of lid 1316 pulls the pad away from stoma 1304. Optionally, absorbing pad 1374 is extracted from ostomy appliance 1300 by removal of cap 1310 or lid 1316. Optionally, the pad is provided with at least one impermeable surface. This provides a potential advantage by preventing soak-through of waste material. Potentially, it is an advantage for sanitary handling when the pad needs to be removed.

In some embodiments, absorbing pad 1374 is attached to pouch 1314 so that deployment of the pouch removes the pad from stoma 1304 and extracts the pad from ostomy device 1300. In some embodiments, absorbing pad 1374 is attached to cap 1310, lid 1316, or pouch 1314 by a string, cable, or other attachment element suitable for pulling on the pad. In some exemplary embodiments, absorbing pad 1374 is made of a relatively highly liquid absorbing material such as, for example, cotton, cellulose, or other material from the group of materials known as super-absorbent polymers, or any combination thereof.

Figure 8:
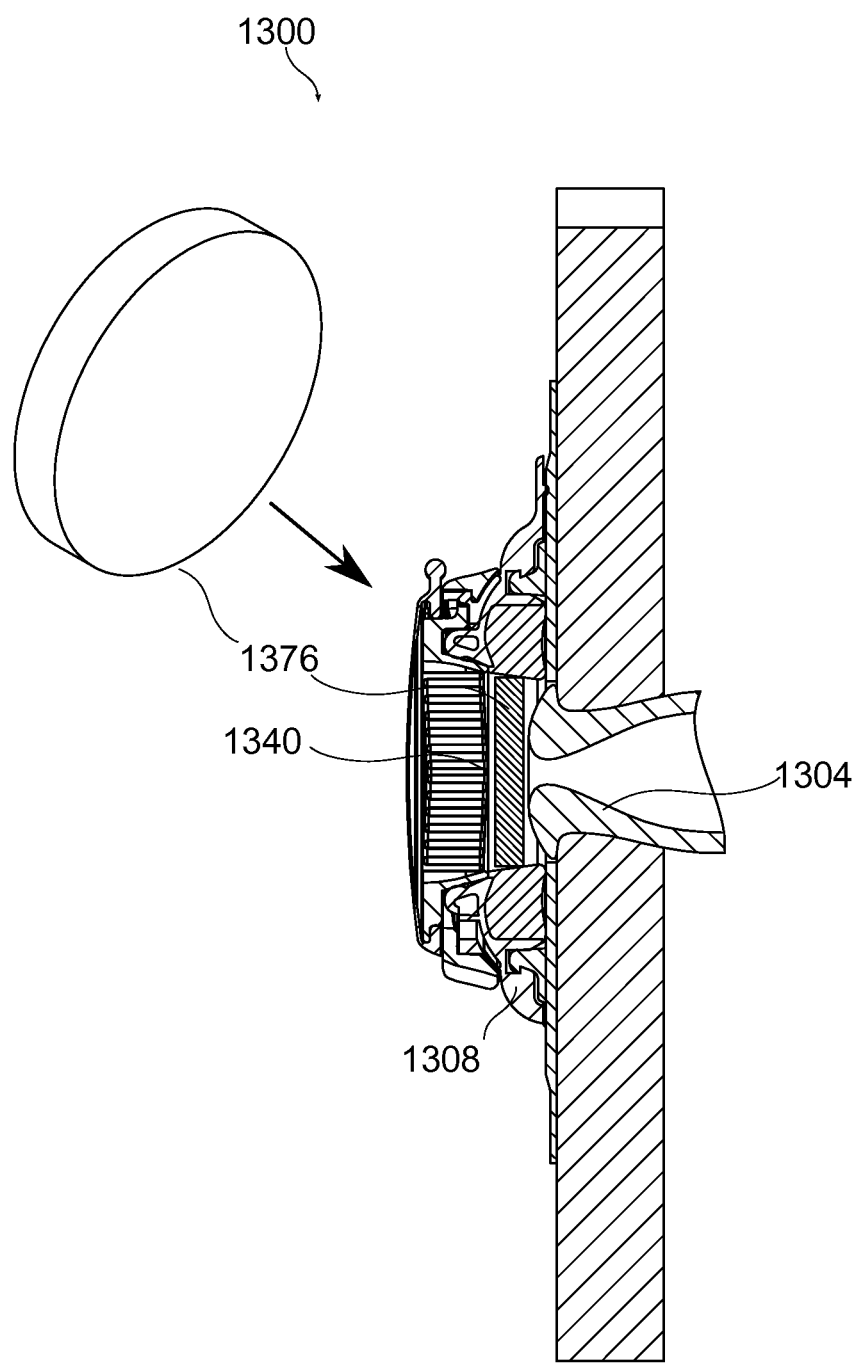
FIG. 8 schematically illustrates a sectional view of an exemplary ostomy appliance attached to a wafer covering the stoma and having an adaptor with a disc-shaped absorbing pad, in accordance with some embodiments of the present invention.
Figure 9:
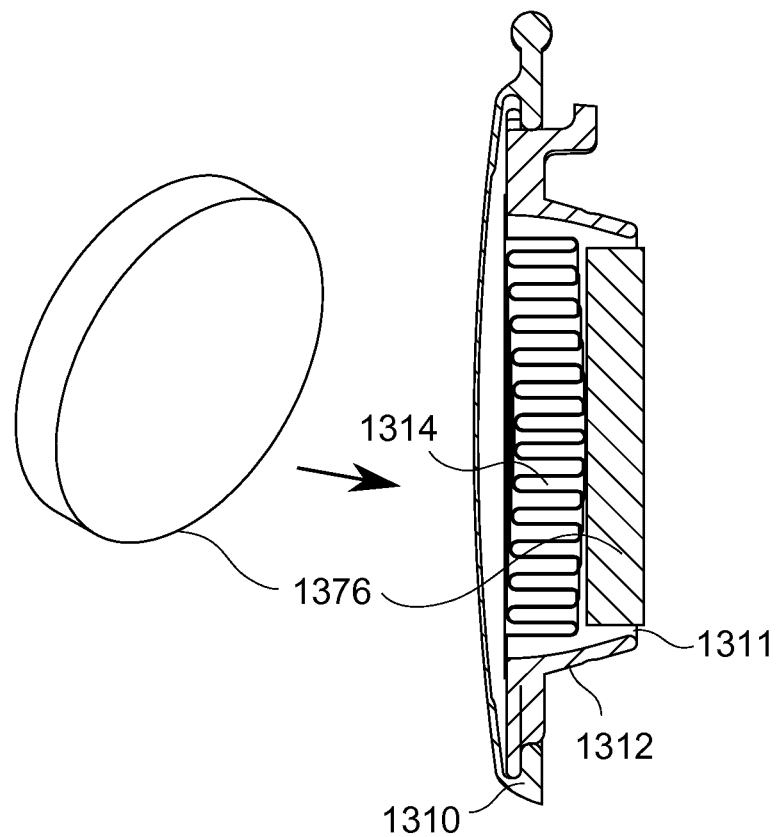
FIG. 9 schematically illustrates a sectional view of an exemplary cap with a disc-shaped absorbing pad, in accordance with some embodiments of the present invention.

In some exemplary embodiments, absorbing pad 1374 is annular in shape, and has a round cross-section, for example as in an O-ring, for peripherally surrounding a circular stoma at wafer/stoma interface 1305. Optionally, the cross-sectional shape of absorbing pad 1374 conforms to the shape of sealing element 1309 at wafer/stoma interface 1305. In some embodiments, absorbing page 1374 is cup shaped, so as to both surround and overlie the stoma. Optionally, a cup-shaped pad is sized so that it surrounds the stoma without contacting it. Additionally or alternatively, absorbing pad is sized to fill portions of cavity 1340, potentially beyond the volume required for simply intercepting waste, so as to reduce free volume and/or internally exposed surfaces. In some embodiments, absorbing pad 1374 has a non-circular cross-sectional shape conforming to the shape of sealing element 1309 at wafer/stoma interface 1305, to the shape of stoma 1304, and/or to the shape of cavity 1340. In some embodiments, adaptor 1308 is fitted with a differently shaped absorbing pad, for example, a disc shape absorbing pad 1376 as shown in FIG. 8. In some embodiments, the absorbing pad is accommodated in cap 1310 inside housing 1312, for example as shown by absorbing pad 1376 in FIG. 9, positioned between pouch 1314 and a distal opening 1311 in the cap. Optionally, another absorbing pad is used inside housing 1312, for example absorbing pad 1374.

Stomal Discharge Restriction

Figure 10:
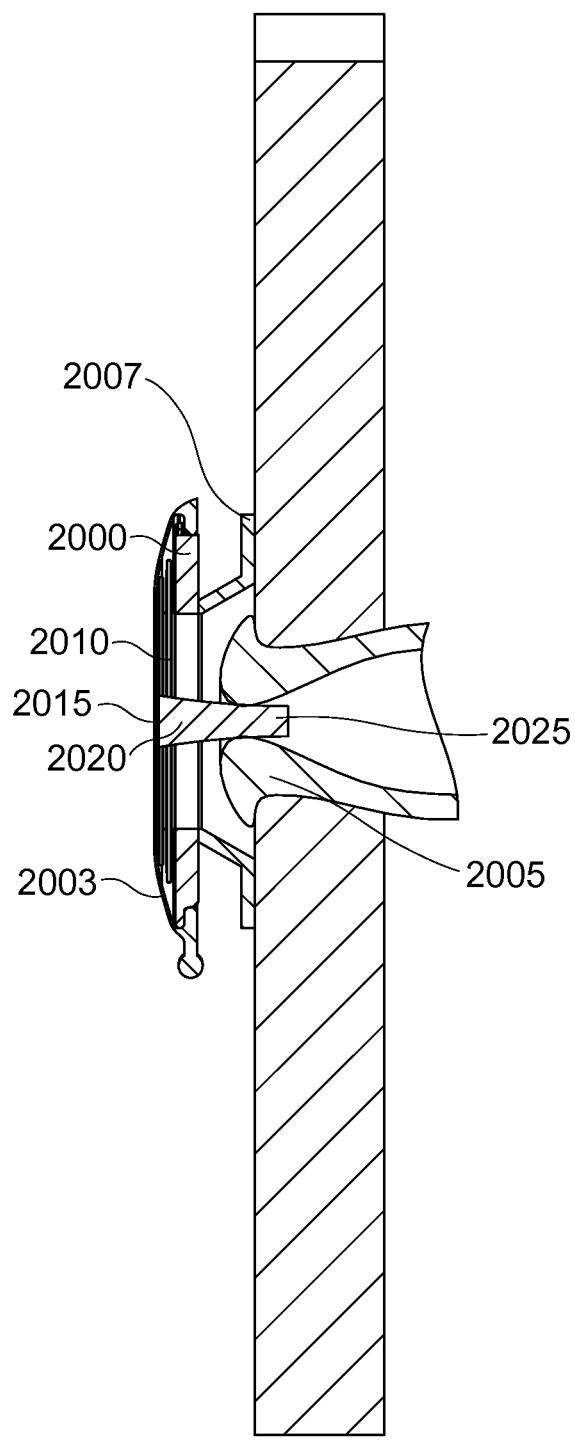
FIG. 10 schematically illustrates a sectional view of an exemplary ostomy cap equipped with a stomal plug, in accordance with some embodiments of the present invention.
Figure 11:
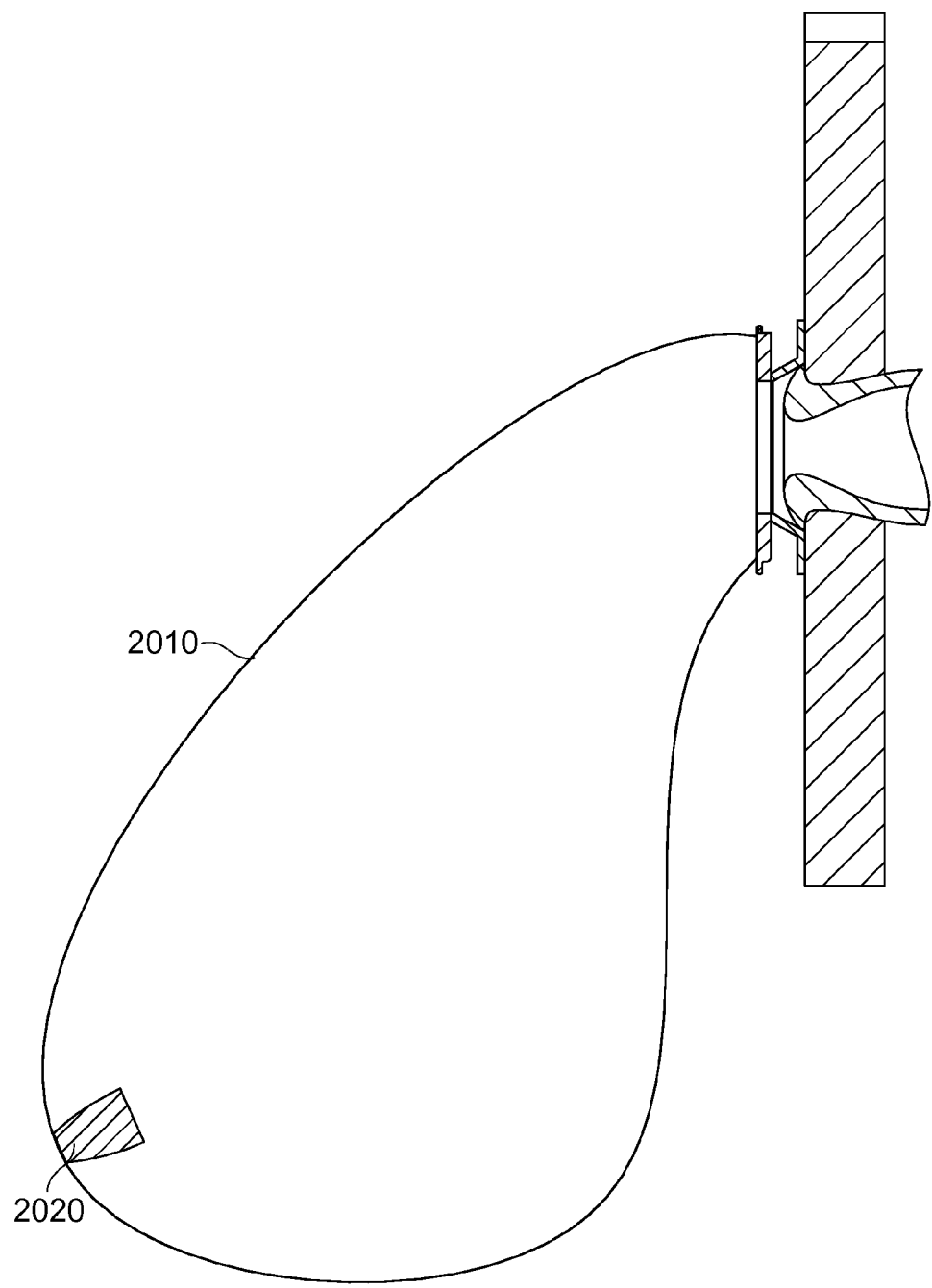
FIG. 11 schematically illustrates a sectional view of an exemplary ostomy cap equipped with a stomal plug, in accordance with some embodiments of the present invention.

Reference is now made to FIGS. 10 and 11, which schematically illustrate sectional views of an exemplary ostomy cap 2000 equipped with a stomal plug 2020, in accordance with exemplary embodiments of the invention.

Auxiliary plugging of the stoma potentially reduces stomal discharge contamination of surfaces that lie outside the stoma, but are enclosed by the ostomy appliance.

In some embodiments of the invention, ostomy cap 2000 is provided with a stomal plug 2020 which is sized and shaped to be inserted into a stoma 2005 while ostomy cap 2000 is worn. In some embodiments of the invention, ostomy cap 2000 is worn attached to an ostomy appliance 2007, for example, an ostomy adaptor and/or ostomy wafer. In some embodiments, stomal plug 2020 inserts into stoma 2005 concomitant with attaching cap 2000 and appliance 2007. In some embodiments, stomal plug 2020 is inserted into the stoma 2005 separately.

In some embodiments, stomal plug 2020 is comprised of material which expands after insertion into stoma 2005, for example compressed fibers or a polymer sponge. Optionally, stomal plug 2020 is initially confined in a film which dissolves in a humid environment, permitting self-expansion. Additionally or alternatively, stomal plug 2020 is made of material which absorbs a portion of the stomal discharge. In some embodiments, distal end 2025 of stomal plug 2020 intrudes past the outer plane of the peristomal skin. Optionally, plug 2020 expands radially and/or longitudinally. In some embodiments, distal end 2025 of the stomal plug seals the stomal aperture without protruding distally past the plane of the peristomal skin.

A potential advantage of an expanding stomal plug 2020 is an improved seal against the stoma 2005. A potential advantage of a less intrusive plug 2020 is reduced tissue irritation. A potential advantage of a more intrusive plug is more complete sealing.

In some embodiments, the stem of stomal plug 2020 exerts pressure on the wall of the stoma which is in the range of, for example: 10-30 mmHg, 80-100 mmHg, 60-200 mmHg, or another range which reaches higher and/or lower pressures. Optionally, an increased pressure on stomal plug 2020, below the pressure required to fully dislodge it, causes plug 2020 to move proximally. In some embodiments, proximal motion of plug 2020 presses against more proximal components of the ostomy appliance, for example, the pouch 2010 and/or pouch restraint 2003. In some embodiments, this causes an indication, such as a bulge, of a need to perform an evacuation. In some embodiments, a pressure exceeding a predetermined threshold dislodges plug 2020. Optionally, dislodgement and/or the pressure needed for dislodgement causes deployment of pouch 2010.

The pressure needed for dislodgement may be set, for example, by the size of the plug. In some embodiments, a user selects a plug size based on the size of their stoma. A potential advantage of a predetermined threshold of pressure to dislodge a stomal plug is to increase safety of the device.

In some embodiments, stomal plug 2020 is comprised of a material, for example cotton, which is permeable to gasses. In some embodiments, stomal plug 2020 allows the passage of flatus while retaining liquid and solid stomal discharge.

A potential advantage of a gas-permeable stomal plug 2020 is to reduce the buildup of internal gasses.

In some embodiments, the proximal end 2015 of stomal plug 2020 is attached to an interior face of a collapsed stomal discharge collection pouch 2010. Optionally, the attachment is direct. Optionally, the attachment is indirect, for example, via a cord, and/or strap (not shown). Attachment is by, for example, adhesive bonding, tying, crimping and/or welding. In some embodiments, and upon removal of pouch restraint 2003, pouch 2010 deploys under a sufficient pressure, dislodging attached stomal plug 2020. In FIG. 11, pouch 2010 is shown deployed, with stomal plug 2020 dislodged from the stoma 2005, but still attached to a portion of the interior bag.

A potential advantage of a secured plug is to avoid the plug 2020 falling into the stoma. A potential advantage of a plug secured to a cord or other long member 2020 is to allow easier separate insertion of the plug and attachment of the ostomy cap 2000.

In some embodiments, ostomy cap 2000 is provided with additional ostomy cap features, for example as described and/or listed herein. Optionally, ostomy cap 2000 is provided with additional cap features known in the art.

Figure 12A:
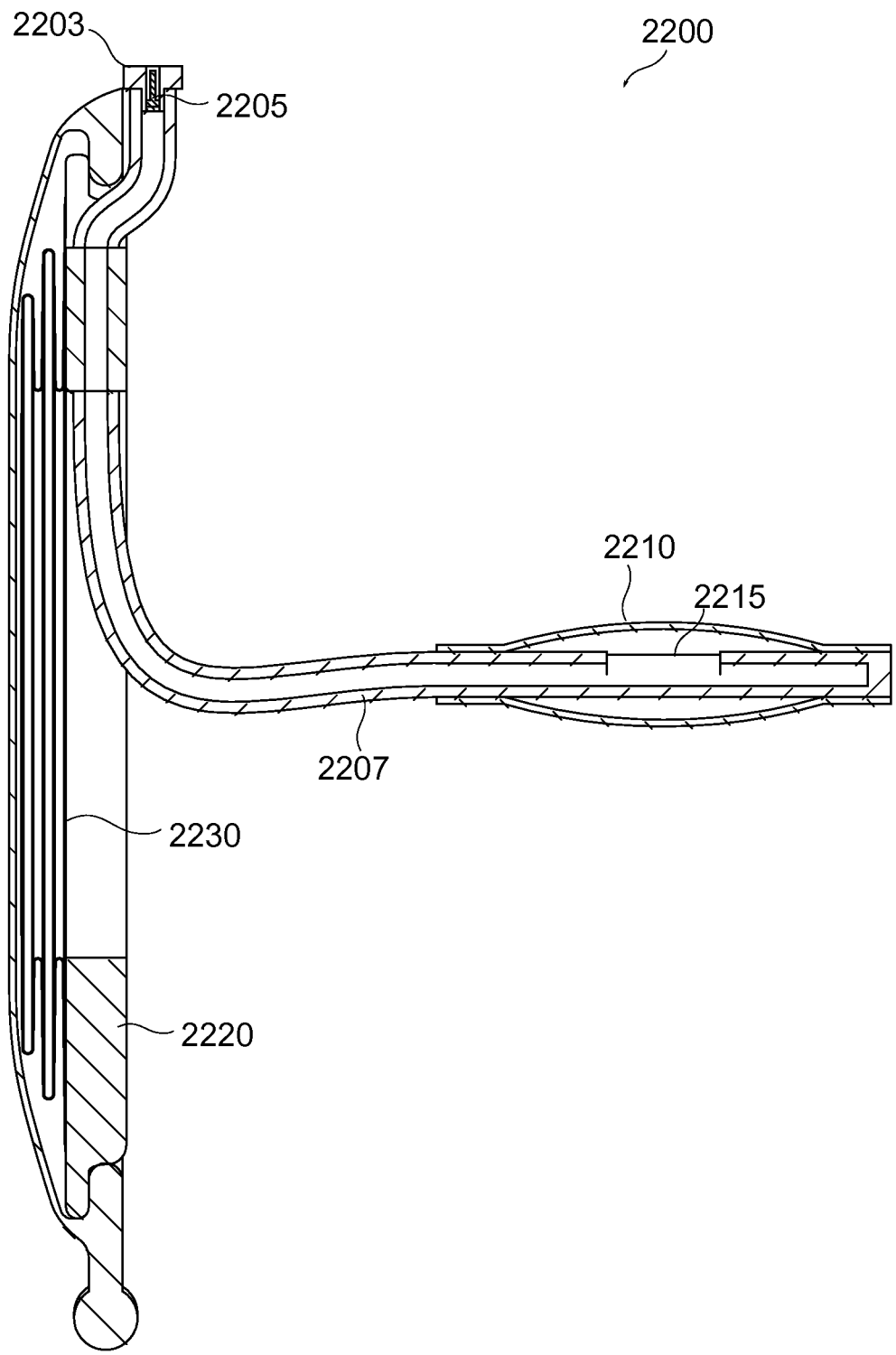
FIG. 12A schematically illustrates a sectional view of an exemplary ostomy cap equipped with an inflatable stomal plug, in accordance with some embodiments of the present invention.
Figure 12B:
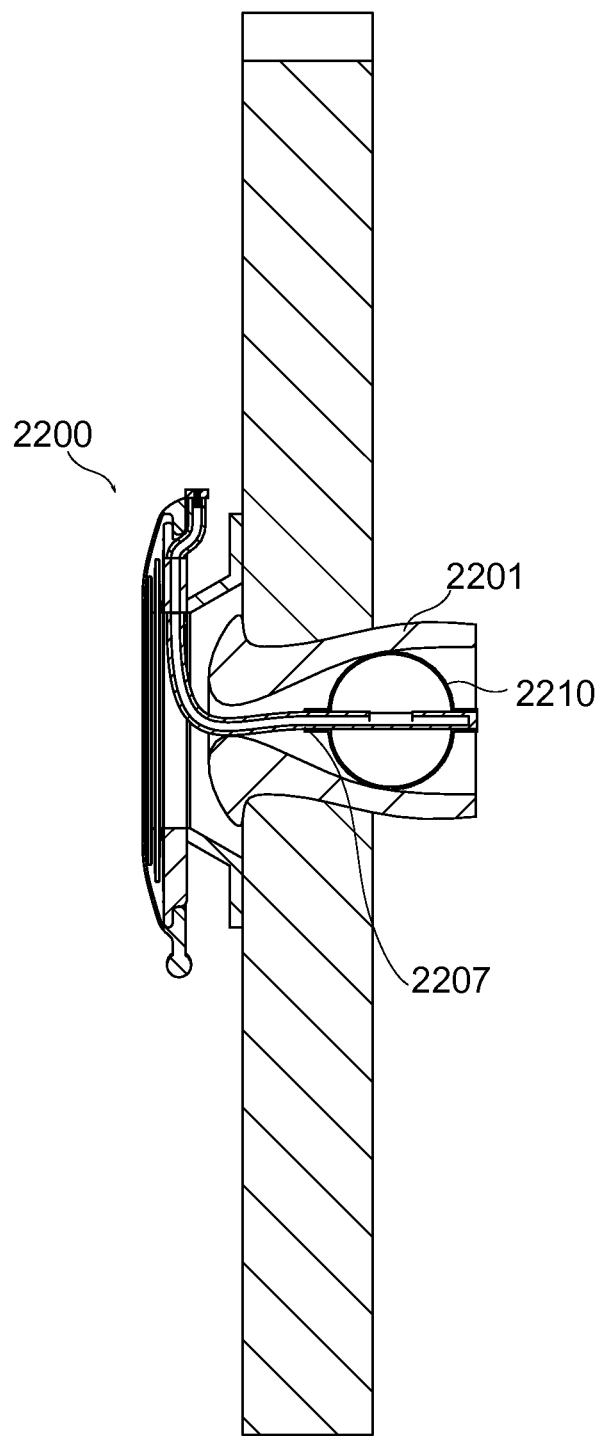
FIG. 12B schematically illustrates a sectional view of an exemplary ostomy cap equipped with an inflated inflatable stomal plug, in accordance with some embodiments of the present invention.
Figure 13:
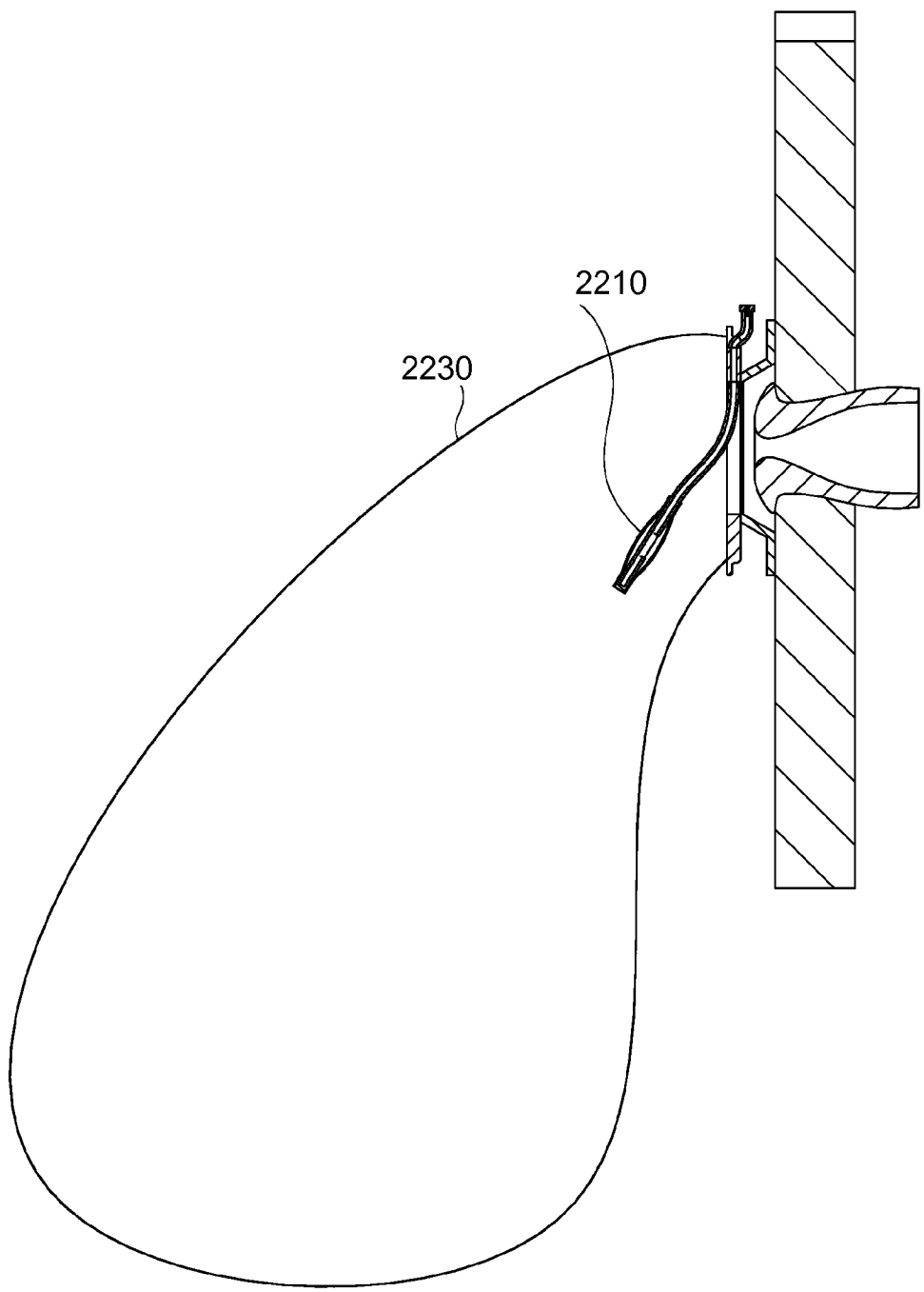
FIG. 13 schematically illustrates a sectional view of an exemplary ostomy cap equipped with an inflatable stomal plug, in accordance with some embodiments of the present invention.

Reference is now made to FIGS. 12A, 12B, and 13, which schematically illustrate sectional views of an exemplary ostomy cap 2200 equipped with an inflatable stomal plug.

In some embodiments of the invention, ostomy cap 2200 is comprised of a cap housing 2220, attached to inflatable balloon 2210 by flexible tubule 2207. In some embodiments, fluid and/or gas under pressure is introduced into tubule 2207 through filling aperture 2203, inflating the balloon when it exits the tubule at distal aperture 2215. Inflation is with, for example, air, water, saline and/or another suitable fluid or gas. In some embodiments of the invention, a valve 2205 serves to maintain pressure in the balloon. In some embodiments, the tubule and/or balloon are formed of flexible material, for example silicone rubber of 20-50 Shore A. In some embodiments, inflated balloon 2210 is adapted to press against the abdominal wall behind the stoma with sufficient force to maintain its position and cause sealing, without damaging the surrounding tissue. Optionally, ostomy cap 2200 comprises the inflation pump and/or inflation fluid or gas source for balloon 2210.

In some embodiments of the invention, the at least partially deflated balloon 2210 is inserted behind the opening of stoma 2201, and inflated in place via tube 2207. The inflated balloon is then an at least partial seal against the stoma interior (FIG. 12B), restricting the flow of stomal discharge.

In some embodiments, opening valve 2205 deflates balloon 2210 and releases sealing. In some embodiments, a sufficient pressure behind the seal leads to deployment of pouch 2210. In some embodiments, balloon 2210 itself is a restraint on deployment of pouch 2210 while it is in place. Optionally, a proximal pouch restraint is used. Optionally, deployment is manual. In some embodiments, balloon 2210 is swept into pouch 2230 during deployment by the force of gaseous, liquid and/or solid stomal discharge. In some embodiments, balloon 2210 is attached to a portion of the pouch that expands proximally when deployed, by a connection short enough that the deployment pulls the balloon into the pouch.

Pouch Restraints

Figure 14A:
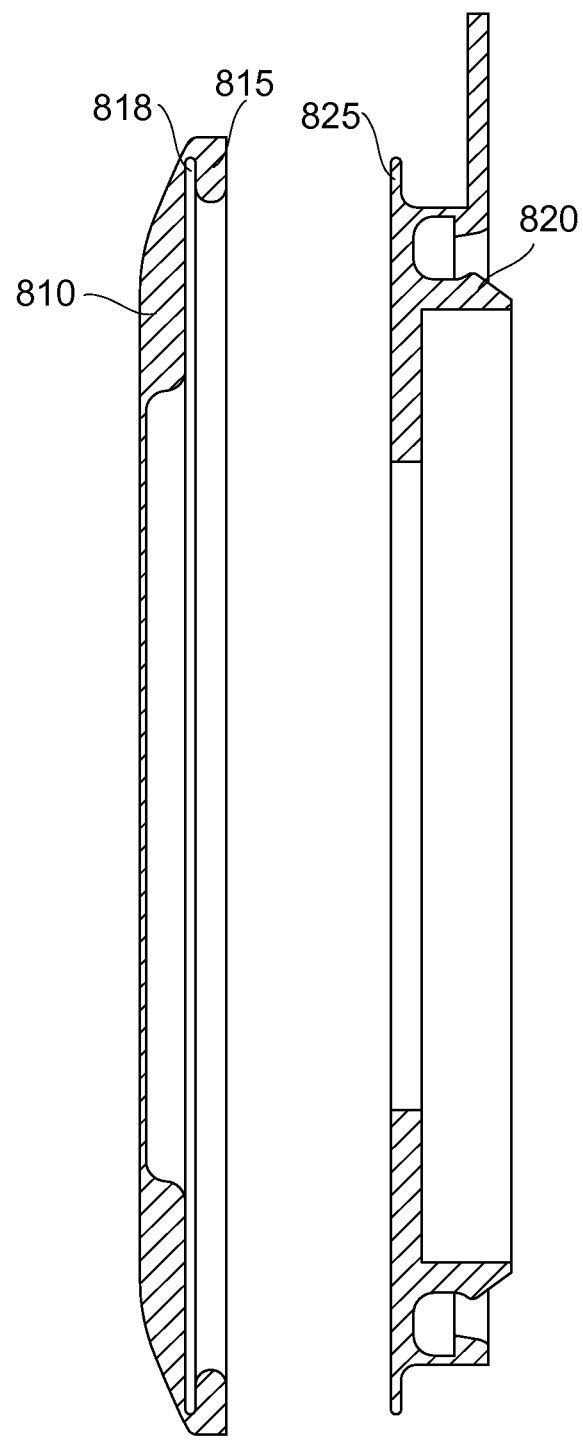
FIG. 14A schematically illustrates a disassembled sectional view of an exemplary ostomy restraint cover attachable to an ostomy component housing, in accordance with some embodiments of the present invention.

Reference is now made to FIG. 14A, which schematically illustrates a disassembled sectional view of an exemplary ostomy restraint cover 810 attachable to ostomy component housing 820. In some embodiments, ostomy component housing 820 is a housing of an ostomy cap. Restraint cover 810 has at least one overhang portion 815 which can attach to corresponding mating flange 825 of housing 820. When assembled, flange 825 occupies recess 818 of restraint cover 810.

The attachment mechanism of a pouch restraint can be designed, for example, to determine pressure release characteristics of the restraint, permitting automatic deployment of a stomal discharge collection pouch.

In some embodiments of the invention, a sufficient pressure from within the ostomy appliance presses at least a portion of restraint cover 810 outward, distorting its shape so that it detaches. The sufficient pressure is set by parameters of the design, for example material and/or geometry, and is, for example 60-100 mmHg, 100-150 mmHg, or 150-200 mmHg, or a larger or smaller range.

Figure 14B:
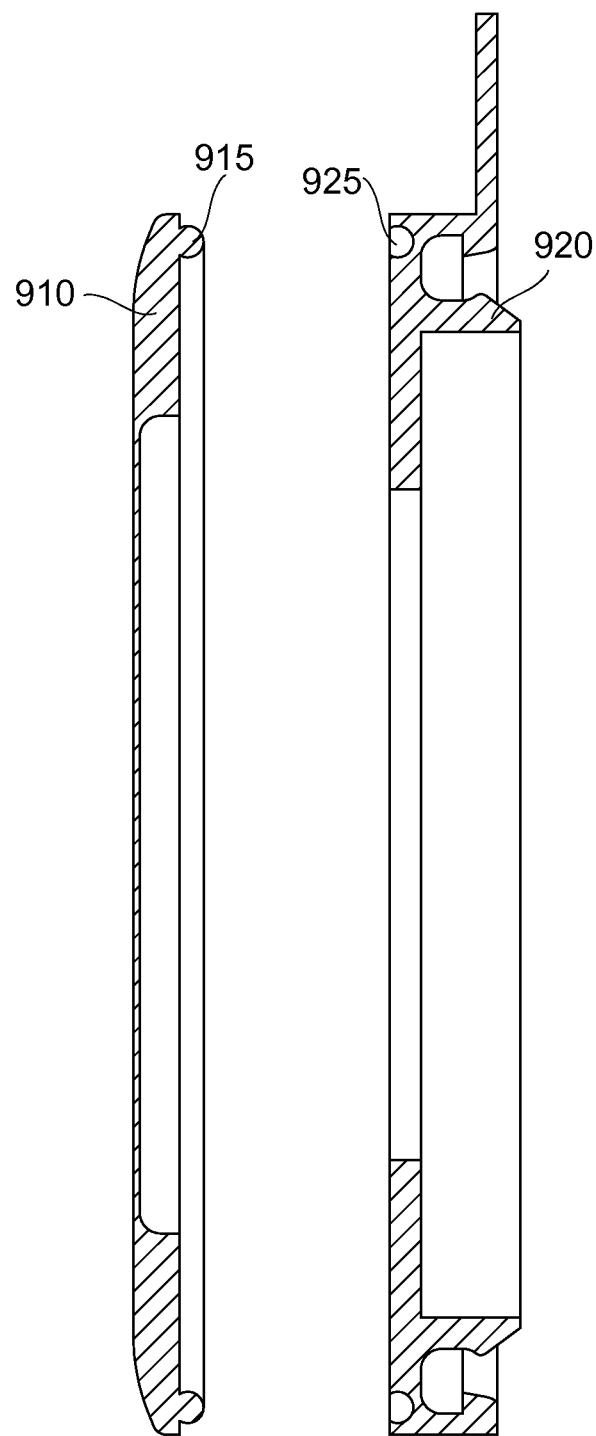
FIG. 14B schematically illustrates a disassembled sectional view of an exemplary ostomy restraint cover attachable to an ostomy component housing, in accordance with some embodiments of the present invention.

Reference is now made to FIG. 14B, which schematically illustrates a disassembled sectional view of an exemplary ostomy restraint cover 910 attachable to ostomy component housing 920.

In some embodiments, ostomy component housing 920 is a housing of an ostomy cap. Restraint cover 910 has at least one bead 915 adapted to attach to corresponding depression 925 of housing 920.

In some embodiments of the invention, a sufficient pressure from within the ostomy appliance presses at least a portion of restraint cover 910 outward so that it detaches. In some embodiments, detachment is as a result of pulling force on the beat distorting it and/or its recess. The sufficient pressure is set by parameters of the design, for example material and/or geometry, and is, for example: 60-100 mmHg, 100-150 mmHg, or 150-200 mmHg, or a larger or smaller range.

A potential advantage of the bead-and-depression attachment mechanism is that restraint cover 910 snaps into place with broad pressure, reducing the need for fine motor control. Another potential advantage is to aid resealing in the event of unwanted partial detachment, for example, due to activities which cause the ostomy appliance to flex. Potentially, a user is able to re-secure the attachment by a broad pressure applied distally, instead of being required to reach under or pinch through clothing.

Returning again to FIGS. 1A and 1B: in some embodiments of the invention, cover 140 is attached to an ostomy appliance component, for example a surface of housing 135, by pressure-breaking attachments formed at regions of contact therebetween, by mechanisms such as adhesive, or breakaway welding. Alternatively, a surface of collapsed pouch 150 is attached to an ostomy appliance component, for example a surface of housing 135, by said pressure-breaking attachments without a cover. In some embodiments, the attachment parameters, for example the type and amount of adhesive or the type and working parameters of welding, are chosen such that under sufficient outward pressure acting on the body of the cover and/or on the collapsed pouch, attachment is broken to permit pouch deployment.

Figure 15A:
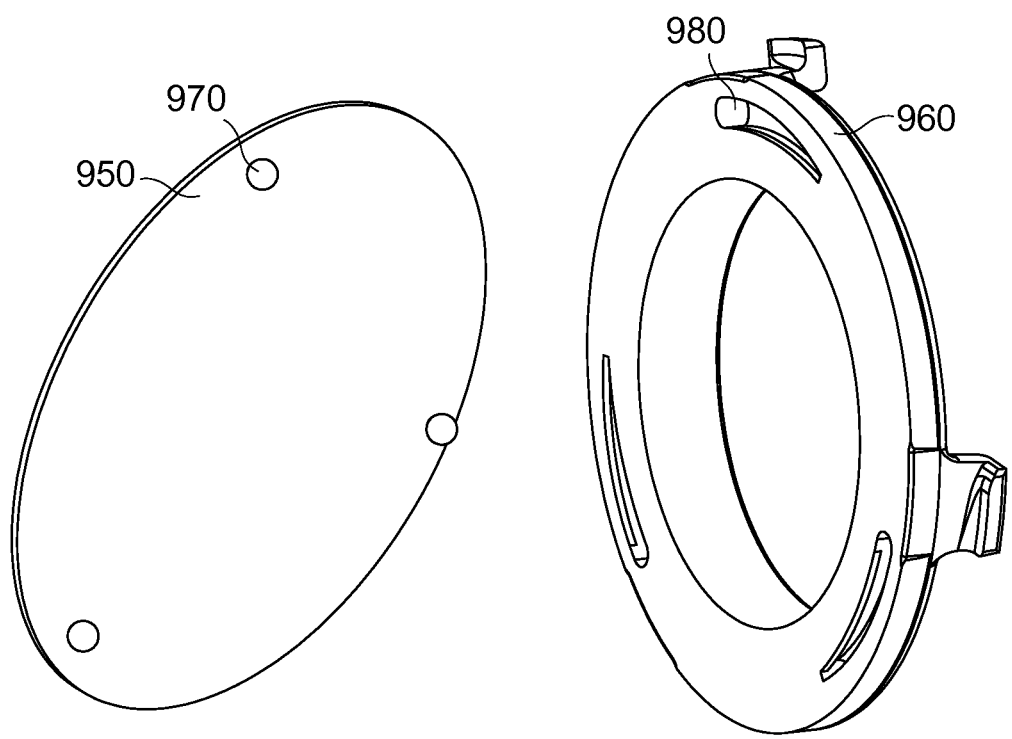
FIG. 15A schematically illustrates a disassembled perspective view of an exemplary ostomy restraint cover attachable to ostomy component housing, in accordance with some embodiments of the present invention.

Reference is now made to FIG. 15A, which schematically illustrates a disassembled perspective view of an exemplary ostomy restraint cover 950 attachable to ostomy component housing 960.

In some embodiments, ostomy component housing 960 is a housing of an ostomy cap. Restraint cover 950 has at least one bead 970 adapted to attach to corresponding depression 980 of housing 960. In some embodiments, depression 980 has a variably-sized cross section, such that the relative size of bead 970 and the region of depression 980 into which it inserts varies depending on the relative positioning of housing 960 and cover 950. This provides a potential advantage by changing the strength of the attachment, allowing a release pressure for cover 950 to be determined by the user.

In some embodiments, relative size variation of attachment elements allowing variable release pressure determination is achieved through other designs. For example, there may be multiple depressions of varying size (allowing discrete release pressure setting). Also for example, beads of varying size may be provided on one of the attaching components, along with one size of fitting depression on the other, and one or more additional depressions which receive unattached beads but are not fitting.

In some embodiments, at least two different sets of attachment elements are formed such that one set detaches at a lower release pressure and one set at a higher release pressure. In some embodiments, the lower release pressure attachment elements comprise a seal against the release of gas from the interior of the ostomy appliance, along with the restraint cover, which in these embodiments covers an aperture completely. For example, the bead and depression attachment mechanism may be formed into a continuous circumference. In some embodiments, the higher release pressure attachment elements are sufficient to retain the restraint cover in place. A potential advantage of having two release pressures is that a buildup of retained gasses, which may not require deployment of a pouch for the collection of waste, can be automatically released without interfering with the restraint function of the restraint cover. It should be noted that realizing this potential advantage may require that a component internal to the ostomy appliance, such as a filter, be configured to allow the passage of gasses bypassing the waste collection pouch, even when the ostomy appliance as a whole is sealed to the outside environment.

It should be noted by someone skilled in the art that the attachment mechanisms discussed in relation to FIG. 14A, FIG. 14B and FIG. 15A are susceptible to variations including but not limited to: swapping the positions of flange and overhang or bead and depression among ostomy component faces; interrupting the continuity of such elements so as to produce more than one flange, overhang, bead, and/or depression; and/or mixing different forms of attachment element on a single component or component surface. The ostomy component to which a restraint cover attaches is not limited to a cap housing, and may be, for example, an portion of a wafer or an ostomy adaptor.

Figure 15B:
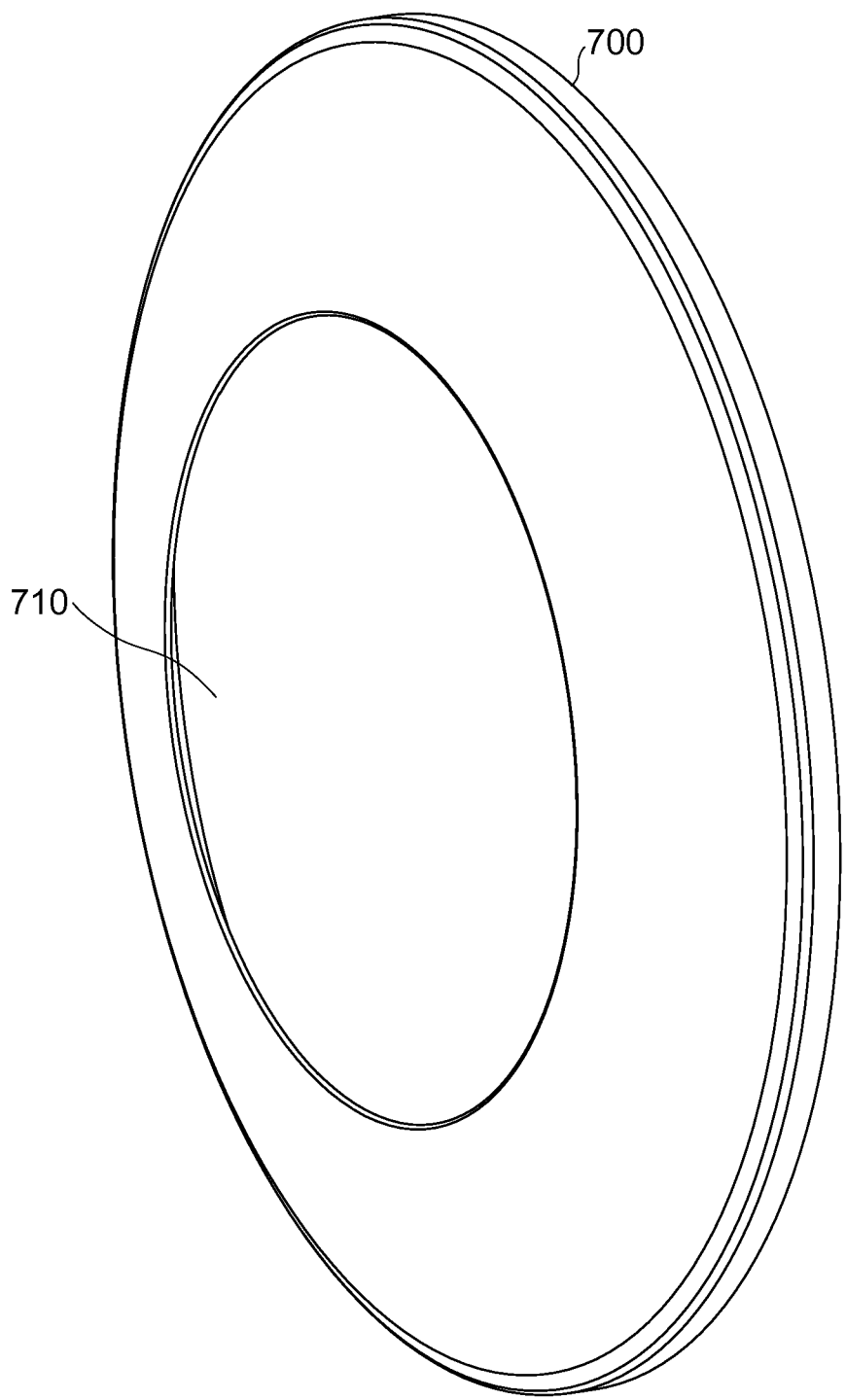
FIG. 15B schematically illustrates a perspective view of an exemplary ostomy cover having an aperture, in accordance with some embodiments of the present invention.

Reference is now made to FIG. 15B, which schematically illustrates an perspective view of an exemplary ostomy cover 700 having an aperture 710, according to some exemplary embodiments of the invention.

In some embodiments of the invention, restraint cover 700 attaches to another component of an ostomy appliance, for example, an ostomy cap housing 135. In some embodiments, while the restraint cover is attached it restrains a collapsed ostomy pouch 160 from fully deploying in response to pressure from the stoma; for example pressure from stomal gasses, liquid stomal discharge, and/or solid stomal discharge. In some embodiments, the restraint cover is attached so that a sufficient pressure from within the ostomy appliance dislodges its attachment. In some embodiments, the restraint cover may be removed manually.

In some embodiments, collapsed pouch 150 is configured to press against the restraint cover 700 under pressure. In some embodiments pouch 150 may be touched and/or viewed through aperture 710. Accordingly, it may serve as a pressure and/or stomal discharge level indicator for a user; for example, through its appearance, degree of compliance when pressed distally, and/or its degree of distension.

Figure 15C:
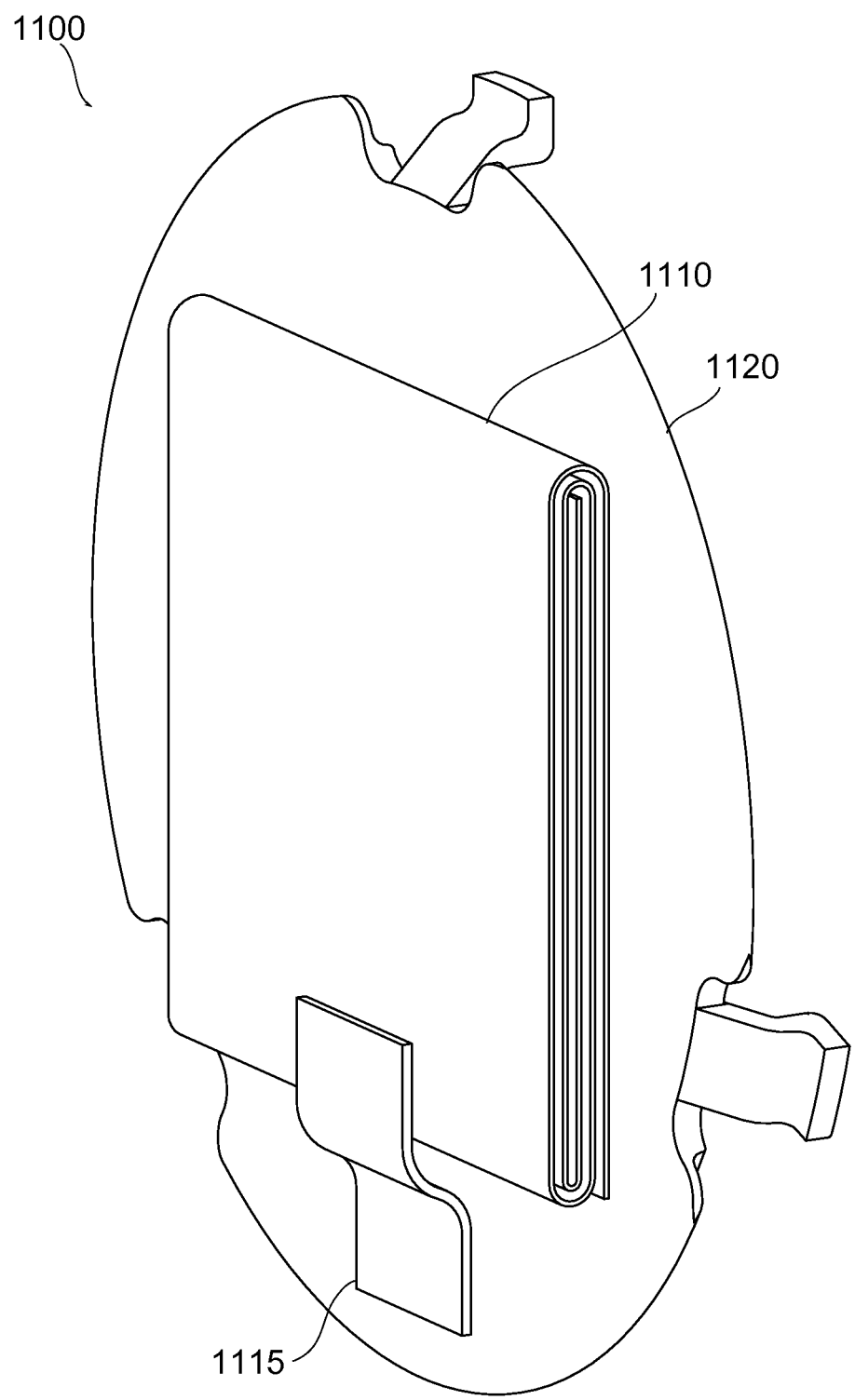
FIG. 15C schematically illustrates a perspective view of an exemplary ostomy cap, having a collapsed stomal discharge collection pouch attached to a cap housing by a pouch restraint strip, in accordance with some embodiments of the present invention.

Reference is now made to FIG. 15C, which schematically illustrates a perspective view of an exemplary ostomy cap 1100, having a collapsed stomal discharge collection pouch 1110 attached to cap housing 1120 by a pouch restraint strip 1115, in accordance with some embodiments of the present invention.

In some embodiments, restraint strip 1115 is a flexible plastic film. In some embodiments, restraint strip 1115 is an adhesive tape. In some embodiments, pouch 1110 is folded.

In some embodiments, one portion of strip 1115 is attached to collapsed pouch 1110, and another portion is attached to the cap housing 1120 and/or another component of the ostomy appliance. The nature of an attachment may be, for example, adhesive, chemically bonded, or welded.

In some embodiments, the attachment and configuration of strip 1115 with pouch 1110 and housing 1120 is such that the pouch cannot deploy unless at least one of the attachments is overcome. Optionally, the attachment may be overcome by manual detachment. Additionally or alternatively, the attachment may be overcome automatically, for example, by a pressure which breaks the attachment.

In some embodiments, collapsed pouch 1110 is configured to receive pressure from within the ostomy appliance it is attached to. This pressure may cause partial filling and/or inflation even while under restraint. Accordingly, collapsed pouch 1110 may serve as a pressure and/or stomal discharge level indicator for a user; for example, through its appearance, degree of compliance when pressed distally, and/or its degree of distension.

A potential advantage of a pouch strip restraint over other restraint embodiments is low cost. Another potential advantage of a strip restraint is the ability to provide a pre-packaged pouch module which requires fewer user steps to install and/or operate. Another potential advantage of a strip restraint is that it is easy to remove and/or to reapply if accidentally detached.

Figure 16A:
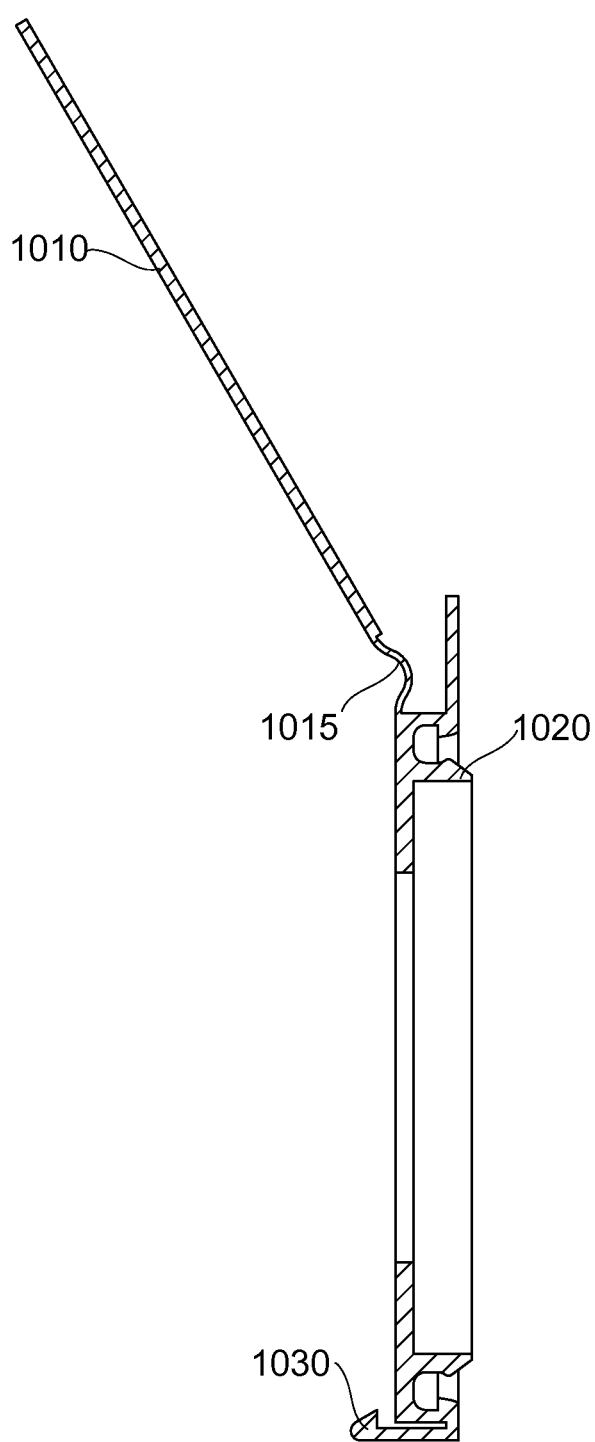
FIG. 16A schematically illustrates a sectional view of an exemplary ostomy component housing, integrally attached to a restraint cover by a hinge, in accordance with some embodiments of the present invention.

Reference is now made to FIG. 16A, which schematically illustrates a sectional view of an exemplary ostomy component housing 1020, integrally attached to a restraint cover 1010 by hinge 1015.

In some embodiments, a hinge member on a restraint permits deployment of a stomal discharge collection pouch, without the restraint cover becoming fully detached from the ostomy apparatus, a condition which may lead to the cover falling to the floor and/or requiring to be held and/or caught during detachment.

In some embodiments of the invention, flanged hook 1030 provides a fastening mechanism which engages with cover 1010 in a closed position, securing it. In some embodiments, a fastening mechanism other than flanged hook 1030 is used, for example a Velcro or an adhesive tape. In some embodiments, a sufficient pressure from within the ostomy appliance makes the fastening mechanism release, allowing restraint cover 1010 to open. The sufficient pressure is set by parameters of the design, for example material and/or geometry, and is, for example 60-100 mmHg, 100-150 mmHg, or 150-200 mmHg, or a larger or smaller range.

Figure 16B:
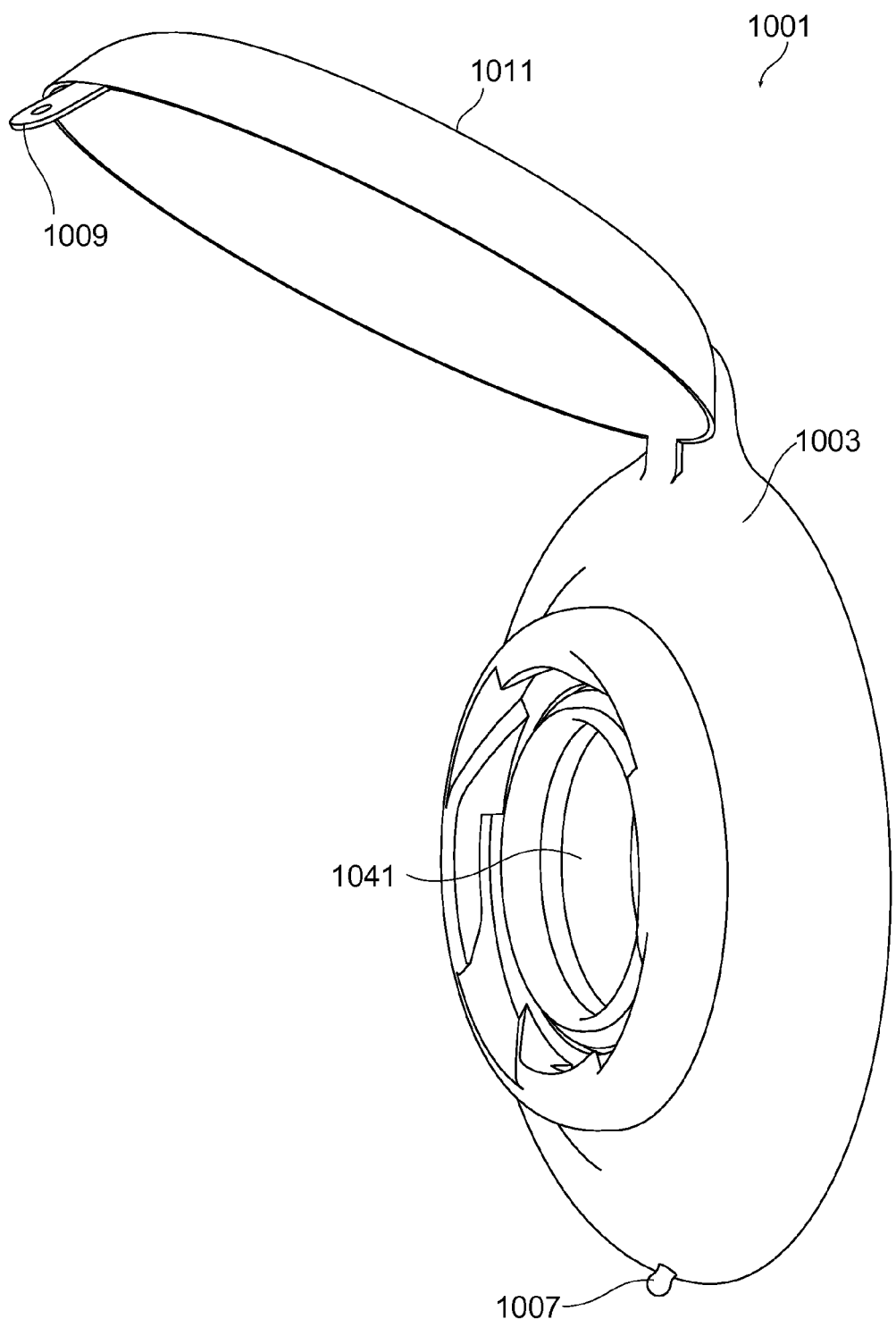
FIG. 16B schematically illustrates a perspective view of an adaptor including an integral cap, in accordance with some exemplary embodiments of the present invention.
Figure 16C:
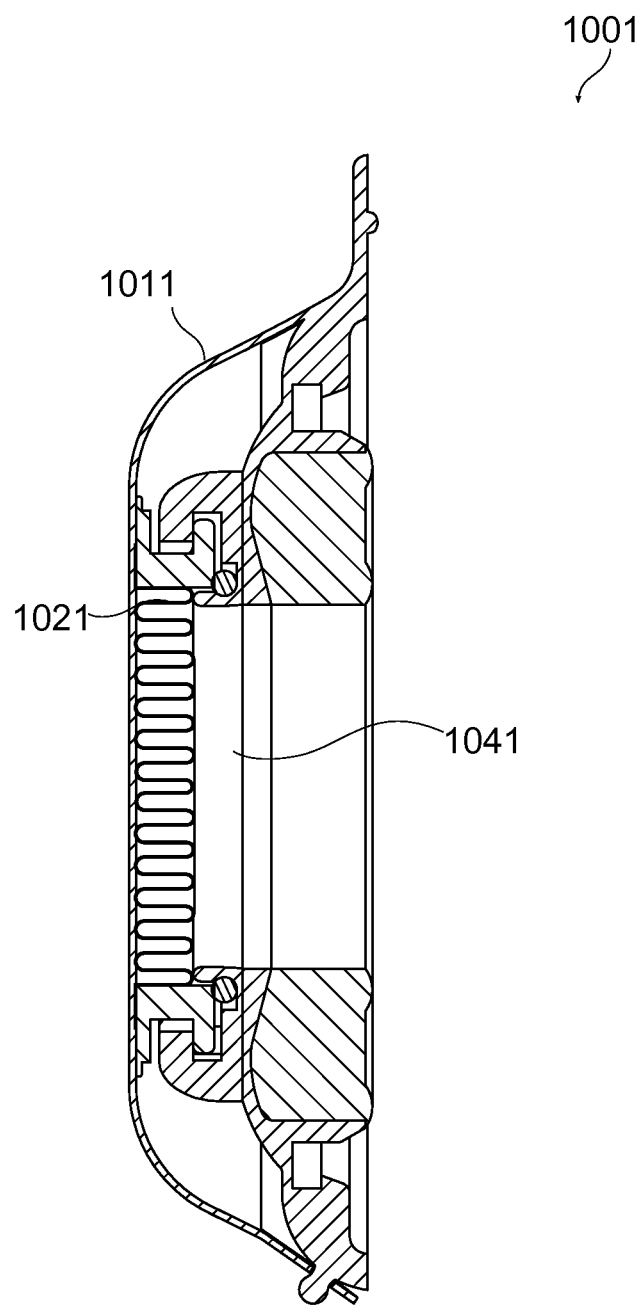
FIG. 16C schematically illustrates a sectional view of the adaptor and the integral cap shown in FIG. 16B, in accordance with some exemplary embodiments of the present invention.

Reference is now made to FIG. 16B which schematically illustrates a perspective view of an exemplary ostomy adaptor 1001 including an integrated pouch restraint cover 1011, and to FIG. 16C which schematically illustrates a sectional view of adaptor 1001 and cover 1011, according to some embodiments of the present invention.

Integrated pouch restraint cover 1011 is fastened to adaptor 1001, for example by means of a hinge, which is, for example, a flexible tab, a hinged pin arrangement, a cable, or other suitable attachment means. Cover 1011 is adapted to cover proximal opening 1041.

In some embodiments, restraint cover 1011 restricts the deployment of collapsed pouch 1021. In some embodiments, restraint cover 1011, for example, assumes a bulge and/or becomes less compliant when pressed distally, serving as a pressure indicator alerting the user of a need to evacuate. In some embodiments, integral cap 1011 seals proximal opening 1041, preventing stomal discharge from flowing or leaking out.

In some exemplary embodiments, adaptor 1001 includes a fastening mechanism including a first mating element 1007 on adaptor body 1003 and a second mating element 1009 on cover 1011 for securing the cap against the adaptor body. Optionally, first mating element 1007 and/or second mating element 1009 are pressure activated by the user for securing 1011 against adaptor body 1003 and/or for releasing the cap from the body.

In some embodiments, a sufficient pressure from within the ostomy appliance makes the fastening mechanism release, allowing restraint cover 1011 to open. The sufficient pressure is set by parameters of the design, for example material and/or geometry, and is, for example: 60-100 mmHg, 100-150 mmHg, or 150-200 mmHg, or a larger or smaller range.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A restraint for a collapsed waste collection pouch of an ostomy appliance, comprising:
    a body; and
    one element of
        at least one pair comprising a receiving aperture and an inserting projection,
        the projection sized to insert into the aperture and form a fitting attachment,
        the other element of the at least one pair being upon the ostomy appliance; such that
        the attached body is positioned to restrain the collapsed pouch from expanding under pressure from within the ostomy appliance to the volume which the unrestrained pouch is rated to contain, wherein the one element is disposed upon the body, and wherein the receiving aperture is a depression on a surface of the body if the receiving aperture is disposed upon the body, or is a depression on a surface of the ostomy appliance if the receiving aperture is disposed upon the ostomy appliance; and
    the strength of the fitting attachment is set so that it breaks when pressed by a pressure from within the ostomy appliance which exceeds a predetermined threshold.

2. The restraint according to claim 1, wherein the restraint is fixedly attached to the ostomy appliance through a flexible member.

3. The restraint according to claim 2, wherein the flexible member is a hinge.

4. The restraint according to claim 1, wherein the elements of the at least one pair are disposed on facing surfaces of the body and the ostomy appliance.

5. The restraint according to claim 4, wherein at least one element of the at least one pair comprising a receiving aperture and inserting projection is of variable size, at least across a profile, such that the relative size of receiving aperture and projection at the place of attachment is selected by the relative positioning of the pair elements.

6. The restraint according to claim 5, wherein the attachment-breaking pressure is different depending on the relative attached positioning of the at least one pair comprising a receiving aperture and inserting projection.

7. The restraint according to claim 1, wherein:
    at least two regions of fitting attachment have attachment broken, each above a different pressure threshold;
    one threshold being higher than the other;
    attachment loss at the lower threshold comprising a loss of resistance to the escape of stomal gasses from the ostomy appliance; and
    attachment loss at the higher threshold comprising loss of restraint on the expansion of the pouch.

8. The restraint according to claim 1, wherein said body is adapted to distend under pressure from said pouch, the distention of said body serving as a pressure indicator for a user of said restraint.

* * * * *